(12) United States Patent
Ideker et al.

(10) Patent No.: US 6,484,057 B2
(45) Date of Patent: Nov. 19, 2002

(54) PACING METHODS AND DEVICES FOR TREATING CARDIAC ARRHYTHMIAS AND FIBRILLATION

(75) Inventors: Raymond E. Ideker; Jonathan C. Newton, both of Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 88 days.

(21) Appl. No.: 09/742,651

(22) Filed: Dec. 21, 2000

(65) Prior Publication Data

US 2002/0123771 A1 Sep. 5, 2002

(51) Int. Cl.[7] .......................... A61N 1/368; A61N 1/05; A61N 1/362

(52) U.S. Cl. .............................. 607/14; 607/4; 607/122
(58) Field of Search ................................ 607/122, 123, 607/4, 14

(56) References Cited

U.S. PATENT DOCUMENTS

| | | | |
|---|---|---|---|
| 3,825,015 A | 7/1974 | Berkovits | 128/404 |
| 3,995,623 A | 12/1976 | Blake et al. | 128/2.06 E |
| 4,355,646 A | 10/1982 | Kallok et al. | 128/786 |
| 4,365,639 A | 12/1982 | Goldreyer | 128/786 |
| 4,444,195 A | 4/1984 | Gold | 128/642 |
| 4,499,907 A | 2/1985 | Kallok et al. | 128/786 |
| 4,559,946 A | 12/1985 | Mower | 128/419 D |
| 4,567,901 A | 2/1986 | Harris | 128/786 |
| 4,637,397 A | 1/1987 | Jones et al. | 128/419 D |
| 4,643,201 A | 2/1987 | Stokes | 128/786 |

(List continued on next page.)

FOREIGN PATENT DOCUMENTS

| | | | |
|---|---|---|---|
| EP | 0095726 B1 | 2/1988 | A61N/1/38 |
| EP | 0472 411 A1 | 2/1992 | A61B/5/07 |
| EP | 0554 208 A2 | 8/1993 | A61B/5/0452 |
| EP | 0 601 340 A1 | 6/1994 | A61N/1/05 |
| EP | 0653223 A2 | 10/1994 | A61N/1/05 |
| EP | 0804938 A2 | 11/1997 | A61N/1/365 |
| WO | WO96/23546 | 8/1996 | A61N/1/39 |
| WO | WO 97/01373 | 1/1997 | A61N/1/39 |
| WO | WO99/65561 | 12/1999 | A61N/1/05 |

OTHER PUBLICATIONS

Allessie et al., "Regional control of atrial fibrillation by rapid pacing in concious dogs," *Circulation* 1991;84:1689–1697.

Capucci et al., "Capture window in human atrial fibrillation: evidence of an excitable gap," *J Cardiovasc Electrophysiol* 1999;10:319–327.

Cooper et al., "Internal Cardioversion of Atrial Fibrillation in Sheep," Atrial Fibrillation: Mechanisms and Therapeutic Strategies, pp. 325–332 (1994).

Cooper et al., "Internal Cardioversion of Atrial Fibrillation in Sheep," Circulation, vol. 87, No. 5, May 1993, pp. 1673–1685.

(List continued on next page.)

*Primary Examiner*—Carl Layno
(74) *Attorney, Agent, or Firm*—Myers Bigel Sibley & Sajovec, P.A.

(57) ABSTRACT

Pacing systems for the heart employ multi-site contact points about desired localized regions to deliver pacing train stimulation pulses to the myocardium. The stimulation pulses can have an electric strength in the range of about 5–10 times the diastolic pacing threshold. The electrodes can be arranged as a single continuous body line electrode or as a plurality of point electrodes and even as contiguous body electrodes occupying increased portions of the myocardium over conventional pacing electrodes. Configuring the electrodes in spaced apart operational pairs (with simultaneous excitation) may capture increased areas of the myocardium. The pacing stimulation may be used as an alternative to conventional defibrillation treatments (shocks) or to reduce the strength of the defibrillation shock pulse.

75 Claims, 13 Drawing Sheets

U.S. PATENT DOCUMENTS

| | | | |
|---|---|---|---|
| 4,693,253 A | 9/1987 | Adams | 128/419 D |
| 4,708,145 A | 11/1987 | Tacker, Jr. et al. | 128/419 D |
| 4,800,883 A | 1/1989 | Winstrom | 128/419 D |
| 4,850,357 A | 7/1989 | Bach, Jr. | 128/419 D |
| 4,901,725 A | 2/1990 | Nappholz et al. | 128/419 |
| 5,107,834 A | 4/1992 | Ideker et al. | 128/419 D |
| 5,165,403 A | 11/1992 | Mehra | 128/419 |
| 5,184,616 A | 2/1993 | Weiss | 128/419 |
| 5,201,808 A | 4/1993 | Steinhaus et al. | 128/419 |
| 5,209,229 A | 5/1993 | Gilli | 128/419 |
| 5,224,476 A | 7/1993 | Ideker et al. | 128/419 D |
| 5,230,337 A | 7/1993 | Dahl et al. | 607/5 |
| 5,235,977 A | 8/1993 | Hirschberg et al. | 607/5 |
| 5,235,978 A | 8/1993 | Hirschberg et al. | 607/5 |
| 5,251,624 A | 10/1993 | Bocek et al. | 607/6 |
| 5,265,623 A * | 11/1993 | Kroll et al. | 607/122 |
| 5,267,559 A | 12/1993 | Jin et al. | 128/419 D |
| 5,269,298 A | 12/1993 | Adams et al. | 128/419 D |
| 5,269,319 A | 12/1993 | Schulte et al. | 128/786 |
| 5,282,836 A | 2/1994 | Kreyenhagen et al. | 607/4 |
| 5,292,338 A | 3/1994 | Bardy | 607/5 |
| 5,303,702 A | 4/1994 | Bonnet et al. | 607/20 |
| 5,304,139 A | 4/1994 | Adams et al. | 607/122 |
| 5,304,218 A | 4/1994 | Alferness | 607/122 |
| 5,312,444 A | 5/1994 | Bocek et al. | 607/5 |
| 5,313,953 A | 5/1994 | Yomtov et al. | 600/508 |
| 5,314,430 A | 5/1994 | Bardy | 607/5 |
| 5,324,309 A | 6/1994 | Kallok et al. | 607/5 |
| 5,331,966 A | 7/1994 | Bennett et al. | 128/696 |
| 5,332,400 A | 7/1994 | Alferness | 607/5 |
| 5,344,430 A | 9/1994 | Berg et al. | 607/8 |
| 5,348,021 A | 9/1994 | Adams et al. | 128/708 |
| 5,350,402 A | 9/1994 | Infinger et al. | 607/5 |
| 5,366,485 A | 11/1994 | Kroll et al. | 607/5 |
| 5,366,486 A | 11/1994 | Zipes et al. | 607/5 |
| 5,387,233 A | 2/1995 | Alferness et al. | 607/126 |
| 5,395,373 A | 3/1995 | Ayers | 607/8 |
| 5,403,351 A | 4/1995 | Saksena | 607/4 |
| 5,403,354 A | 4/1995 | Adams et al. | 607/5 |
| 5,405,375 A | 4/1995 | Ayers et al. | 607/122 |
| 5,411,527 A | 5/1995 | Alt | 607/5 |
| 5,423,772 A | 6/1995 | Lurie et al. | 607/282 |
| 5,431,681 A | 7/1995 | Helland | 607/4 |
| 5,431,682 A | 7/1995 | Hedberg | 607/5 |
| 5,431,683 A | 7/1995 | Bowald et al. | 607/5 |
| 5,433,729 A | 7/1995 | Adams et al. | 607/5 |
| 5,433,730 A | 7/1995 | Alt | 607/5 |
| 5,441,519 A | 8/1995 | Sears | 607/5 |
| 5,443,491 A | 8/1995 | Snichelotto | 607/122 |
| 5,447,519 A | 9/1995 | Peterson | 607/5 |
| 5,456,706 A | 10/1995 | Pless et al. | 607/122 |
| 5,464,429 A | 11/1995 | Hedberg et al. | 607/4 |
| 5,464,432 A | 11/1995 | Infinger et al. | 607/4 |
| 5,470,348 A | 11/1995 | Neubauer et al. | 607/68 |
| 5,476,498 A | 12/1995 | Ayers | 607/122 |
| 5,476,499 A | 12/1995 | Hirschberg | 607/123 |
| 5,486,199 A | 1/1996 | Kim et al. | 607/5 |
| 5,487,753 A | 1/1996 | MacCarter et al. | 607/17 |
| 5,489,293 A | 2/1996 | Pless et al. | 607/5 |
| 5,522,853 A | 6/1996 | Kroll | 607/5 |
| 5,531,764 A | 7/1996 | Adams et al. | 607/5 |
| 5,554,176 A | 9/1996 | Maddison et al. | 607/9 |
| 5,560,369 A | 10/1996 | McClure et al. | 128/704 |
| 5,578,064 A | 11/1996 | Prutchi | 607/19 |
| 5,584,865 A | 12/1996 | Hirschberg et al. | 607/5 |
| 5,609,621 A | 3/1997 | Bonner | 607/122 |
| 5,620,471 A | 4/1997 | Duncan | 607/14 |
| 5,683,429 A | 11/1997 | Mehra | 602/14 |
| 5,697,953 A | 12/1997 | Kroll et al. | 607/5 |
| 5,713,944 A * | 2/1998 | Kroll | 607/122 |
| 5,718,718 A | 2/1998 | Kroll et al. | 607/5 |
| 5,800,465 A * | 9/1998 | Thompson et al. | 607/9 |
| 5,800,469 A | 9/1998 | Nappholz | 607/18 |
| 5,800,470 A | 9/1998 | Stein et al. | 607/20 |
| 5,861,012 A | 1/1999 | Stroebel | 607/28 |
| 5,978,704 A | 11/1999 | Ideker et al. | 607/123 |
| 5,978,705 A | 11/1999 | KenKnight et al. | 607/5 |
| 5,987,354 A | 11/1999 | Cooper et al. | 607/5 |
| 6,002,962 A | 12/1999 | Huang et al. | 607/5 |
| 6,006,131 A | 12/1999 | Cooper et al. | 607/5 |
| 6,148,230 A | 11/2000 | KenKnight | 600/516 |
| 6,345,198 B1 * | 2/2002 | Mouchawar et al. | 607/4 |

OTHER PUBLICATIONS

Daoud et al. "Response of Type I atrial fibrillation to atrial pacing in humans," Circulation 1996;94:1036–1040.

Feeser et al., "Strength–Duration and Probability of Success Curves for Defibrillation with Biphasic Waveforms," *Circulation*, vol. 82, No. 6, Dec. 1990, pp. 2128–2141.

García–Calvo et al., "The effects of selective stellate ganglion manipulation on ventricular refractoriness and excitability," PACE, 1992;15:1492–1503.

Huang et al., "Evolution of the organization of epicardial activation patterns during ventricular fibrillation," J Cardiovasc Electrophysiol, 1998;9:1291–1304.

KenKnight et al., "Regional capture of fibrillating ventricular myocardium: Evidence of an excitable gap," Circ Res 1995;77:849–855.

Kirchhof et al., "Regional entrainment of atrial fibrillation studied by high–resolution mapping in open–chest dogs," Circulation 1993;88:736–749.

Knisley et al., "Line stimulation parallel to myofibers enhances regional uniformity of transmembrane voltage changes in rabbit hearts," Circ Res 1997;81:229–241.

Kroll, Mark W., "A Minimal Model of the Monophasic Defibrillation Pulse," PACE, vol. 16, Apr. 1993, Part I, pp. 769–777.

Lammers et al., "The use of fibrillation cycle length to determine spatial dispersion in eletrophysiologic properties used to characterize the underlying mechanism of fibrillation," 2 N. Trends Arrhythmia, 1986;2:109–112.

Laxer et al., "The use of computer animation of mapper cardiac potentials in studying electrical conduction properties of arrhythmias," In: Murray A and Arzbaecher R, eds. Proc. Computers in Cardiology, Los Alamitos, CA: IEEE Computer Society Press, Piscataway, NJ, pp. 23–26, (1991).

Lewalter et al., "The Low Intensity Treadmill Exercise" Protocol for Appropriate Rate Adaptive Programming of Minute Ventilation Controlled Pacemakers, PACE, 18:1374–1387 (Jul. 1995).

Lüderitz et al., "Nonpharmacologic Strategies for Treating Atrial Fibrillation," The American Journal of Cardiology, vol. 77, Jan. 25, 1996, pp. 45A–52A.

Opthof et al., "Dispersion of refracteries in canine ventricular myocardium: Effects of sympathetic stimulation," Circ Res 1991;68:1204–1215.

Province et al., "Effect of pulse train amplitude and waveform on ability to entrain fibrillating rabbit ventricle with epicardial pacing," PACE, 22:A66 (1999) (Abstract).

Rogers et al., "A quantitative framework for analyzing epicardial activation patterns during ventricular fibrillation," Ann Biomed Eng 1997;25:749–760.

Rogers et al., "Recurrent wavefront morphologies: a method for quantifying the complexity of epicardial activation patterns," Ann Biomed Eng 1997;25:761–768.

Rollins et al., "Macintosh based programmable cardiac stimulatr," J Am Coll Cardiol, 15:261A (1990) Abstract.

Wharton et al., "Cardiac potential and potential gradient fields generated by single, combined, and sequential shocks during ventricular defibrillation," Circulation 1992; 85:1510–1523.

Wiggers, C.J., "Studies of ventricular fibrillation caused by electric shock: Cinematographic and electrocardiographic observations of the natural process in the dog's heart: Its inhibition by potassium and the revival of coordinated beats by calcium," Am Heart J 1930;5:351–365.

Wolf et al., "A 528 channel system for the acquisition and display of defibrillation and electrocardiographic potentials," In: Murray, A. and Arzbaecher, R., eds. Proc. Computers in Cardiology, Los Alamitos, CA: IEEE Computer Soc. Press, pp. 125–128 (1993).

Wright et al., "Cardiac Rhythm Management Laboratory: In Vivo Study Protocol, Internal Atrial Defibrillation in Sheep Using Sequential Biphasic Waveforms," CRM Laboratory, University of Alabama—Birmingham Medical Center, Oct., 1995.

PCT International Search Report, International Application No. PCT/US01/47195 dated Jul. 23, 2002.

* cited by examiner

MIN. SIZE OF RE-ENTRY CIRCUIT

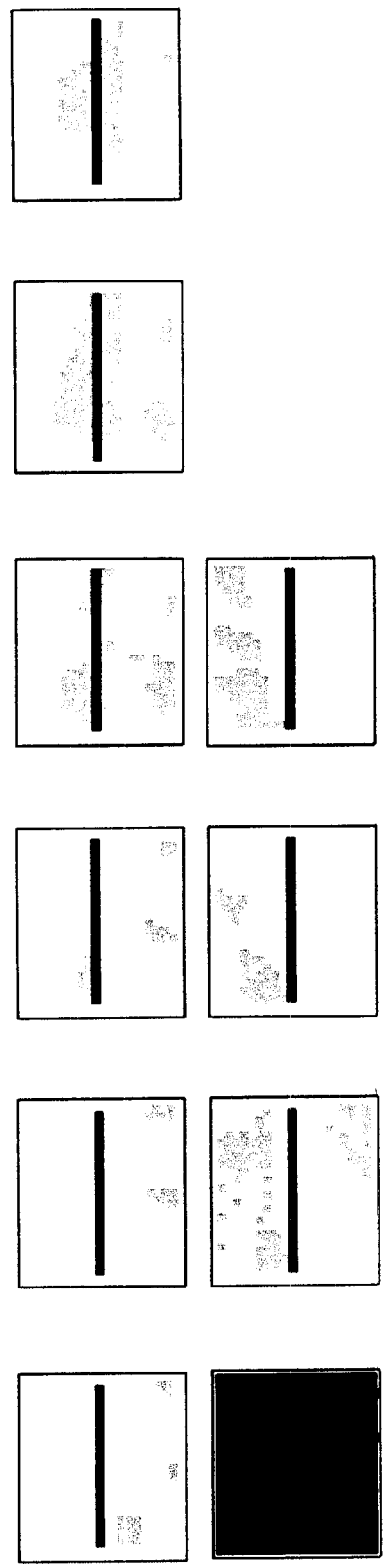

PACING METHODS AND DEVICES FOR TREATING CARDIAC ARRHYTHMIAS AND FIBRILLATION

GRANTS

The invention was supported in part by National Institutes of Health Research Grant HL-28429. The United States Government has certain rights to this invention.

FIELD OF THE INVENTION

The present invention is related to methods and apparatus for treating arrhythmias such as atrial and/or ventricular fibrillation in subjects.

BACKGROUND OF THE INVENTION

The heart is a muscular organ which is covered by a fibrous sac known as the pericardium. The space between the pericardium and the muscular organ is called the pericardial space. The walls of the heart are substantially formed from muscle (the myocardium) which differs from either skeletal or smooth muscle. The heart comprises atria and ventricles, each of which is composed of layers of myocardium which are formed to encase the blood-filled chambers. In operation, when the walls of a chamber contract, they come together similar to a squeezing fist. This contraction of the cardiac muscle is triggered by depolarization of the muscle membrane. To operate properly, the muscle contractions should be coordinated.

If the muscle contractions are not coordinated within the ventricles, blood may be sloshed back and forth within the ventricular cavities instead of being ejected into the aorta and pulmonary arteries. Thus, the complex muscle masses forming the ventricular pumps should contract substantially simultaneously for efficient pumping.

The heart is able to achieve this coordination because of (a) the tight junctions formed between adjacent cardiac fibers (the fibers are joined end to end at structures known as intercalated disks, which provide the points or junctions) which allow action potentials to be transmitted from one cardiac cell to another; and (b) the specialized muscle fibers in certain areas of the heart which provide the conducting system for proper excitation of the heart. The specialized fibers are in contact with fibers of the cardiac muscles to form gap junctions, which permit passage of action potentials from one cell to another. The specialized conduction system is configured, in normal operation, to provide a rapid and coordinated spread of excitation.

Cardiac muscle cells are autorhythmic, i.e., capable of spontaneous, rhythmical self-excitation. The sinoatrial (SA) node is the normal pacemaker for the entire heart or smooth muscle, and it is from this region that the excitation wave starts; it then moves or propagates through the remainder of the myocardium in a synchronized manner. The SA node region of the heart contains a small mass of specialized myocardial cells in the right atrial wall near the entrance of the superior vena cava which have a fast inherent rhythm, which allows the SA node to be the normal pacemaker. In unusual circumstances, other regions of the heart can become more excitable and provide a faster spontaneous rhythm. In this situation, this other region can become the pacemaker and the rhythm for the entire heart.

In normal operation, the cells of the SA node make contact with the surrounding atrial myocardium fibers. Thus, from the SA node, a wave of excitation spreads throughout the right atrium along the atrial myocardial cells via the gap junctions. In addition, the specialized conducting system directs the impulse from the SA node directly to the left atrium, to simultaneously contract both atria.

The excitation wave then is distributed to the ventricles by way of a second small mass of specialized cells located at the base of the right atrium near the wall between the ventricles (the atrioventricular (AV) node). The AV node is configured to delay the propagation of action potentials (the wavefront) by about 0.1 second, to allow the atria to contract and empty the blood into the ventricle before ventricular contraction. The wavefront is then quickly dispersed along the specialized conducting fibers (down the interventricular septum) and then through unspecialized (typical) myocardial fibers in the remaining myocardium.

The pumping of blood includes alternate periods of contraction and relaxation. The cardiac muscle has a relatively long refractory period (on the order of about 250 ms). This refractory period is a time during which the membrane is insensitive to stimulus (either totally unable to propagate an excitation wave or only able to do so upon exposure to an increased level of stimulation).

During ventricullar fibrillation (VF) a number of independent activation wavefronts propagate simultaneously through the mycodardium. It has been suggested that as soon as the myocardium becomes excitable, it is excited by a wandering wavefront. See Lammers et al., *The use of fibrillation cycle length to determine spatial dispersion in eletrophysiologic properties used to characterize the underlying mechanism of fibrillation*, 2 N. Trends Arrhythmia, pp. 109–112 (1986); Opthof, et al., *Dispersion of refracteries in canine ventricular myocardium: Effects of sympathetic stimulation*, 68 Circ. Res., pp. 1204–1215 (1991). This proposition would indicate that there is no excitable gap between activations and would preclude the possibility of capturing fibrillation with exogenously generated electrical stimuli. However, pacing stimuli have been shown to be able to capture the myocardium during fibrillation. For example, Allesie et al and Kirchhof et al. report successful pacing of the canine left atrium during atrial fibrillation; and Daoud et al. and Capucci et al. report successful pacing of the human right atrium during atrial fibrillation. Others report pacing of right ventricular free wall during VF, although capture of the fibrillating myocardium was only successful in about 36% of the episodes. See KenKnight et al., *Regional capture of fibrillating ventricular myocardium: Evidence of an excitable gap*, 77 Circ. Res. 849–855 (1995). In addition, in the past, the amount of myocardium captured by pacing via a single electrode has been relatively modest.

SUMMARY OF THE INVENTION

The present invention provides improved methods and devices for pacing the heart by increasing the number of pacing sites. Certain embodiments of the pacing systems of the present invention include a plurality of discrete electrodes, a single elongated electrode, or one or more line electrodes, arranged to direct at least one pacing train to multiple sites within a selected localized region or regions of the myocardium during a treatment window such as during an episodic onset of an arrhythmia or during a fibrillating event (whether in the atria, the ventricles, or both). In certain embodiments, the present invention can provide a plurality of pacing trains which transmit stimulation pulses to multiple proximately located sites in the myocardium at the time of the onset of a sensed or detected arrhythmia or fibrillation event. In certain embodiments, the timing and/or strength of the pacing trains and the position of the electrodes which transmit the stimuli may improve the likelihood that the arrhythmia will be halted and/or that fibrillating myocardium will be captured.

The pacing train stimuli can be configured with sufficient strength to control the excitation of the heart in the region undergoing stimulation. In certain embodiments, the pacing trains are sequentially delivered and each has an increased electrical strength (increased current) which is well above the lowest electrical stimulation needed to excite the myocardium in the region of interest during diastole of paced or sinus rhythm. In some embodiments, a diastolic pacing threshold (DPT) can be predetermined in situ (DPT is the lowest strength which is able activate the tissue during diastole of paced or sinus rhythm) and for pacing, a 5×–10× DPT stimulation strength can be employed.

Certain embodiments of the present invention are configured, by electrode placement and/or the selection of pacing signals, so that at least a 30–40 mm$^2$ region proximate the stimulus per pacing cycle may be captured, and typically the captured area is between 40 mm$^2$–200 mm$^2$ and higher (such as about 500 mm$^2$, or even up to about the area of substantially the entire myocardium).

One aspect of the invention is a method of pacing to treat arrhythmia in a patient, comprising the steps of: (a) positioning at least one line electrode in a localized region of the heart of a patient such that it covers multiple pacing sites over a distance of between about 0.25–15 cm; and (b) delivering a first pacing stimulation pulse train comprising a plurality of excitation pulses to the at least one electrode to the corresponding multiple pacing sites to pace the myocardium of the patient.

In some embodiments, the first pacing train is delivered responsive to the onset of a fibrillation event. The method can also include the step of delivering a second and/or third pacing train comprising a plurality of excitation pulses to the plurality of sites after the first delivering step. In other embodiments, the method can include the step of administering a pharmacological agent to the patient to increase the degree of organization and/or the step of delivering a defibrillation shock pulse to the patient proximate in time to (including before or during) the fibrillation event. In addition, or alternatively, a defibrillation pulse can also be delivered after pacing and/or with a pharmacological agent.

The present invention may also sense cardiac activity so as to adjust one or more of the pacing stimulation parameters of the pacing stimulation pulse (such as duration, strength, rate, and the like). The sensing information may also be used to delay the delivery of the stimulation until a desired degree of organization is indicated (such as a degree of regularity of cycle intervals).

The present invention can provide a pacing system for the heart of a subject which includes a pulse generator configured to generate at least one, and in at least some embodiments, a plurality of pacing trains, each pacing train having a plurality of stimulation pulses; a power source operably associated with the pulse generator; and at least one electrode configured to pace over multiple sites in one or more localized regions of the myocardium (such as an elongated line electrode or a plurality of electrodes) operably associated with the pulse generator and adapted, in operation, to reside about a localized region of the myocardium so as to be able to pace over multiple pacing sites. The electrodes may be carried on a catheter of mounted on a lead wire and positioned at the desired target region in the heart. The system may also include a detector to sense various cardiac activity such as the onset of an irregular cardiac condition (and/or the intrinsic pacing cycle). The electrodes can be configured to operate with increased resistivity (to be equal to or greater than the resistivity of the myocardium). This may include resistance added in series or parallel arrangements between the pulse generator and the electrode to help balance or reduce the edge effects of the electrode arrangement.

In certain embodiments, the plurality of electrodes can be arranged on one or more line electrodes and the electrodes can be arranged to transmit the pacing train stimuli to the myocardium at the prospective contact points at different sites substantially concurrently. In some embodiments, the electrodes can be configured to transmit the pacing train stimuli in operative spaced apart electrode pairs. The electrodes can be held on two substantially parallel spaced apart line electrodes positioned in at least one localized region of the heart so that the electrodes contact the myocardium. Using two or more electrode pairs (in spaced apart proximity so as to be able to act together to limit reentry circuits) may increase the amount of capture area over that attributed to two electrode systems acting apart.

Another pacing system for the heart of a subject is similar to the one described above, but the electrode can be configured as a line electrode having a contiguous or solid body elongated electrode having a length of between about 0.25–15 cm (and more typically above about 0.5–1 cm to about 15 cm) adapted, in operation, to reside about a localized region of the myocardium.

Another aspect of the invention is a pacing stimulation pulse sequence, comprising a first pacing train having a plurality of excitation pulses at an electrical strength of between about 5–10×DPT; and a second pacing train having a plurality of excitation pulses at an electrical strength of between about 5–10×DPT. The first and second pacing trains are transmitted to a region of the myocardium to pace the excitation of the heart. The pacing stimulation can be transmitted to portions of myocardium where the refractory period is short or the defibrillation shock has a weak effect and/or including sites of ventricular fibrillation (VF) maintenance such as rotors reentrant loops, and sites of focal activity.

The present invention now allows pacing from several proximate sites (via multiple contact points) within a localized region or regions, alone, or in conjunction with the delivery of a defibrillation shock to treat fibrillation. To treat atrial or ventricular fibrillation, the pacing train stimuli may be sized and delivered to the myocardium in a manner which can capture sufficient tissue such that substantially all reentrant circuits capable of maintaining fibrillation are eliminated thereby potentially eliminating the need for the use of defibrillation shocks under some conditions.

Multi-site pacing (via one or more contiguous body (line) electrodes or a plurality of adjacently aligned electrodes) may also be used with the administration of pharmacological agents to increase the degree of organization so that pacing can capture larger regions or so that the number of reentrant circuits is reduced. It is also anticipated that pacing during fibrillation may be combined with conventional defibrillation techniques so that a lower strength shock can be used to defibrillate. This may be accomplished by pacing in areas of myocardium where the defibrillation shock has its weakest effect. It is anticipated that pacing may control activation in this area so that it stops with the termination of pacing, and, thus, the shock strength can be decreased to a strength needed to halt fibrillation in the remaining portions of the myocardium not captured by pacing. This technique may synchronize these defibrillation shocks with respect to the pacing so that the defibrillation shock itself does not re-induce fibrillation in the region captured by pacing. These types of defibrillation treatment methods may be particularly suitable for atrial fibrillation, because they may be able to reduce the discomfort associated with the strong shocks conventionally needed to halt the atrial fibrillation.

The foregoing and other objects and aspects of the present invention are explained in detail in the specification set forth below.

BRIEF DESCRIPTION OF THE DRAWINGS

FIGS. 17A–C are screen printouts of activation fronts during two episodes of pacing from a line of electrodes across the middle of the plaque during VF with a 10×cathodal stimulus. Each snapshot is 8 ms apart in FIG. 17A and 10 ms apart in FIGS. 17B and 17C.

DESCRIPTION OF PREFERRED EMBODIMENTS

Figure 1:
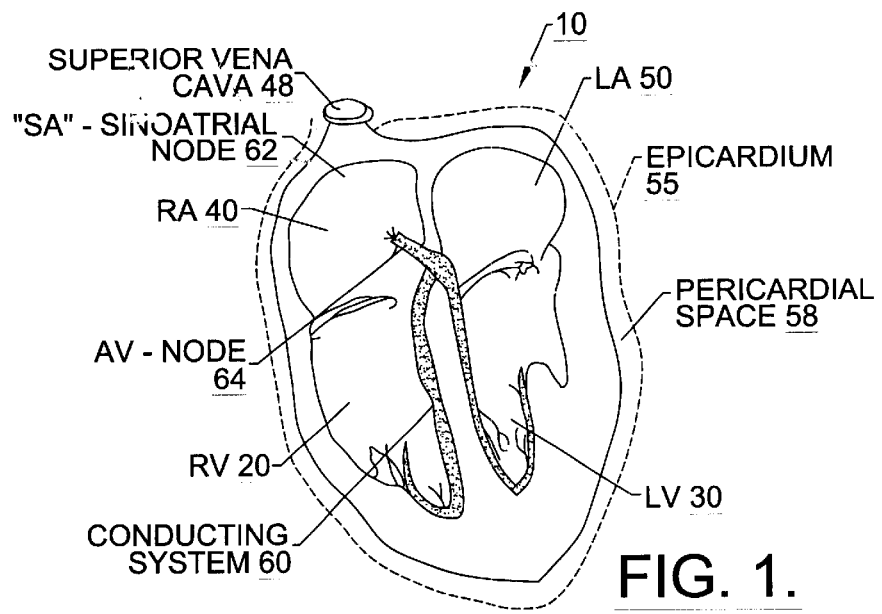
FIG. 1 is a schematic illustration of a human heart.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the figures, layers, components, or features may be exaggerated for clarity.

The present invention may be used for pacing the heart for treating (including preventing or halting) all forms of cardiac tachyarrhythmias in subjects, including antitachycardia pacing to prevent or halt ventricular tachycardia, pacing to prevent or halt ventricular fibrillation, atrial flutter, and atrial fibrillation. The present invention may be particularly suitable for pacing during ventricular fibrillation and/or atrial fibrillation. Certain embodiments of the present invention may be able to control a volume of myocardium and reduce or even eliminate fibrillation within this volume.

Subjects according to the present invention can be any animal subject, are preferably mammalian subjects (e.g., humans, canines, felines, bovines, caprines, ovines, equines, rodents, porcines, and/or lagomorphs), and more preferably are human subjects.

Certain embodiments of the pacing system of the present invention employ a plurality of discrete small or miniaturized electrodes arranged to contact proximately located pacing sites in a desired localized region or regions of the heart. The electrodes can be independently operable and physically separate "point" electrodes or can be arranged in electrical series for "group" operation, such as on a line electrode. Other embodiments can employ a single continuous (elongated) body, line electrode or a contiguous elongated length of electrode to deliver the pacing stimulus across a desired portion of a targeted localized region. Combinations of these electrode configurations and other configurations may also be employed. Electrode configurations will be discussed further below.

In any event, the pacing system is configured to deliver or direct at least one, and in some embodiments, a plurality of sequentially generated, pacing trains (each pacing train providing a plurality of pacing stimuli excitation signals) to multiple proximate sites within a localized region or regions of the myocardium at a desired treatment time(s), such as during a fibrillating event (whether in the atria, the ventricles, or both). Certain embodiments of the pacing systems of the present invention can be configured so that the pacing trains are delivered to each of the electrode(s) in the localized region substantially concurrently or simultaneously. The pacing systems of the present invention can provide or deliver the pacing trains at one or more of before, at the onset of, or during a sensed irregular condition, as well as responsive to a detected arrhythmia or fibrillation event, or even by external activation (such as by the patient or physician). Early activation in connection with the onset of the irregularity may improve the likelihood that the arrhythmia will be prevented or halted and/or that fibrillating myocardium will be able to be successfully captured.

As used herein, a region is considered "captured" when the activations in that region (or the entire heart) are caused by the electrical stimuli, and these activations are substantially phase-locked with the delivery of the stimuli. Stated differently, a region can be considered "captured" when an activation front emanating from or near the pacing site, spreads away from the pacing site, typically, in a substantially similar pattern cycle to cycle (over most cycles). The non-captured regions may continue fibrillating and the activations therein are not phase-locked with the stimuli artifacts. As known to those of skill in the art, phase-locked refers to a regular interval on an electrogram between the stimulus-induced artifact and the onset of activation.

Figure 2:
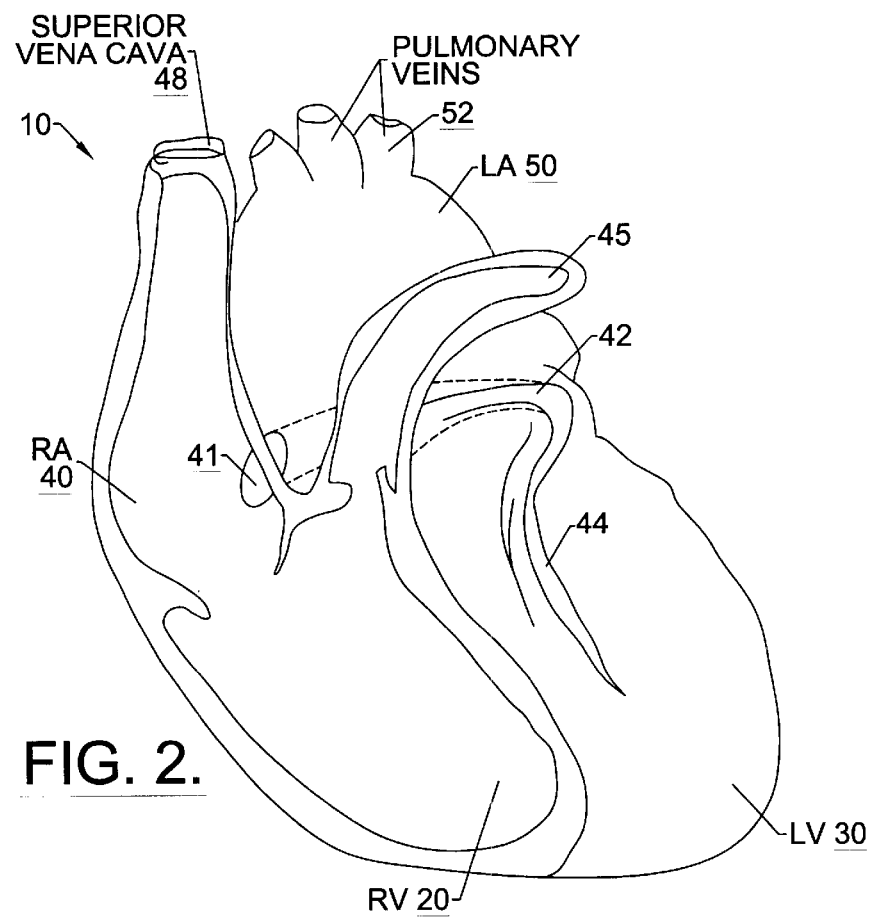
FIG. 2 is a schematic illustration of a human heart.

Anatomically, the heart includes a fibrous skeleton, valves, the trunks of the aorta, the pulmonary artery, and the muscle masses (myocardium) of the cardiac chambers (i.e., right and left atria and right and left ventricles). The schematically illustrated portions of the heart 10 shown in one or more of FIGS. 1 or 2 include the right ventricle "RV" 20, the left ventricle "LV" 30, the right atrium "RA" 40 (the term "right atrium" herein including the superior vena cava and innominate vein), the left atrium "LA" 50 (and parts thereof), the superior vena cava 48, the coronary sinus "CS" 42, the great cardiac vein 44, the left pulmonary artery 45 (the term "left pulmonary artery" herein includes the main pulmonary artery and the right ventricular outflow tract), and the coronary sinus ostium or "OS" 41. FIG. 1 also illustrates the epicardium 55 (shown in dotted line) surrounding the walls of the heart (i.e., the myocardium) and the pericardial space 58 therebetween. FIG. 2 also illustrates the pulmonary veins 52 and neighboring regions. Other regions of interest may include the atrial septum, right and left atrial appendages, and the tricuspid annulus. FIG. 1 also illustrates the conducting system 60, the SA node 62 and the AV node 64.

The desired localized region(s) selected for placement of the electrodes and/or pacing the heart according to the instant invention may vary depending on the physiology or ailment of the patient. As such, the electrodes may be positioned in a number of regions and by a number of different techniques so that they are proximate to and/or in contact with the desired localized region of the myocardium. For example, the electrodes can be positioned in the natural lumens of the heart (atriums, ventricles, veins, arteries, etc.), or in the pericardial space, on the outer, inner surfaces of the cardiac walls, or within the thickness of the muscle walls. As such, the electrodes may be positioned into the body of the subject by surgical techniques or by inserting them using locating catheters holding same, and the like. In certain embodiments, the electrodes are configured and sized such that each is able to contact the tissue at a respective stimulation site during the heartbeats.

Thus, as noted above, the pacing electrodes may be positioned in the pericardial space or other localized regions of the heart. For example, the pacing electrode(s) can be held on a catheter and inserted into the endocardium or threaded through the heart and inserted into the veins in the heart (threaded through the OS and looped into the veins). In some embodiments, pacing of the left atrium may be performed by locating an electrode(s) to extend in a portion of the left atrium and into the pulmonary vein(s) to help eradicate or control fibrillation activation in this region. Locating one or more electrodes in the pulmonary veins may be particularly suitable for the treatment of atrial fibrillation. Other exemplary placements are discussed below.

As described above, the driving force for the flow of blood in the heart comes from the active contraction of the cardiac muscle. This contraction can be detected as an electrical signal. The cardiac contraction is triggered by electrical impulses traveling in a wave propagation pattern which begins at the cells of the SA node and the surrounding atrial myocardial fibers then travels into the atria and subsequently passing through the AV node and, after a slight delay, into the ventricles. Sensing cardiac activation or contractions while pacing can provide data to the pacing system (controller or cardiac monitor) which can be assessed to determine and adjust, as needed, a number of operational parameters such as, for example: (a) when to stop the pacing stimulation; (b) the speed or rate of the pacing stimulation (increase or decrease the pacing rate), the duration or intensity of the stimulation pulse(s); (c) whether the tissue is being successfully captured; and (d) the number of pulses/pulse trains to be relayed to the localized region.

In some embodiments, capture may be more successful if the pacing stimulus is delayed to be transmitted when the arrhythmia is more organized (based on the regularity of AF or VF, or a substantially constant or stable interval between activations). If the intrinsic interval is relatively stable (such as at about 75–1 10% of the mean of the previous 3–15 pulses), then the pacing train stimulus treatment can be initiated. If the timing between pulses is irregular, then the pacing train stimulation can be withheld or delayed. This delayed treatment may be particularly suitable for non-ventricular fibrillating events.

Figure 3:
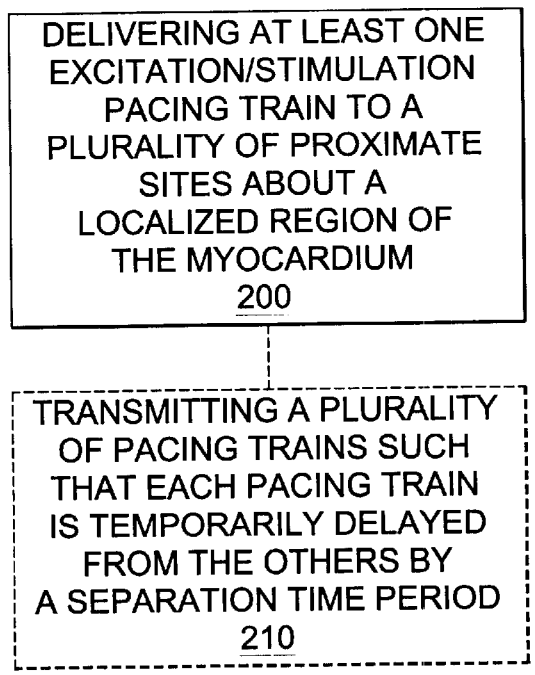
FIG. 3 is a block diagram of the steps of a method for pacing the human heart according to certain embodiments of the present invention.

Referring now to the block diagram of FIG. 3, as described above, the pacing methods and systems for certain embodiments of the present invention include delivering one, or a plurality of pacing train stimulation excitation or stimulation pulses, to a plurality of (adjacent or proximate) sites within a localized region (or regions) of the myocardium (Block 200). Typically, the electrode configuration has a length sufficient to cover a length of from about 0.25–15 cm, as will be described further below. The pacing stimulation can be delivered by a plurality of discrete electrodes, or an elongated or contiguous length of electrode to cover the desired targeted localized pacing region. If a plurality of pacing trains are used, each of the plurality of pacing trains can be separated from the others by a separation time period (Block 210). The pacing trains will be discussed further below.

"Localized" means that the electrical pacing train stimuli are delivered to a portion of the heart rather than to the entire heart, the portion from which the (exogenously generated) stimulated pacing is desired to be initiated. Thus, a pacing stimulus signal is relayed to multiple adjacent sites in a targeted localized region. In certain embodiments, the electrode(s) can occupy a length of space "L" (the length "L" is shown, for example, in FIGS. 7, 8 and 11) of about 0.25–15 cm in size, and preferably at least about 0.5–1 cm to about 15 cm, typically from about 1–5 cm, in the desired localized region. The length of the stimulation electrode can be arranged or oriented in a number of suitable arrangements, such as in substantially linear vertical or longitudinal, or horizontal direction, or diagonally, or in a curvilinear or grid-like manner, or otherwise arranged within the localized region or regions.

Figure 4:
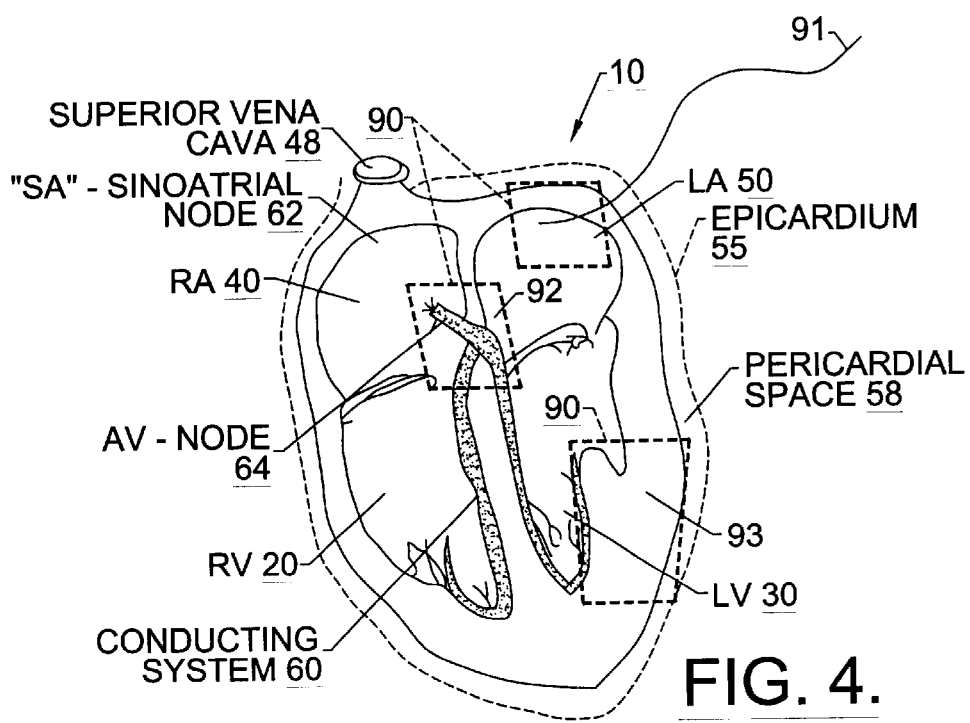
FIGS. 4–5 are schematic illustrations of a human heart showing localized pacing regions according to embodiments of the present invention.
Figure 5:
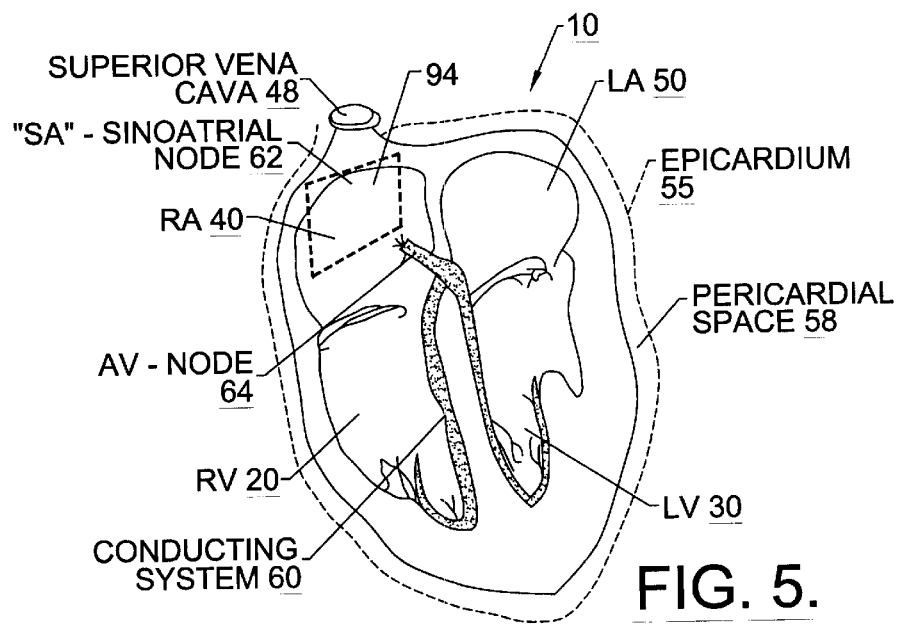
Figure 6:
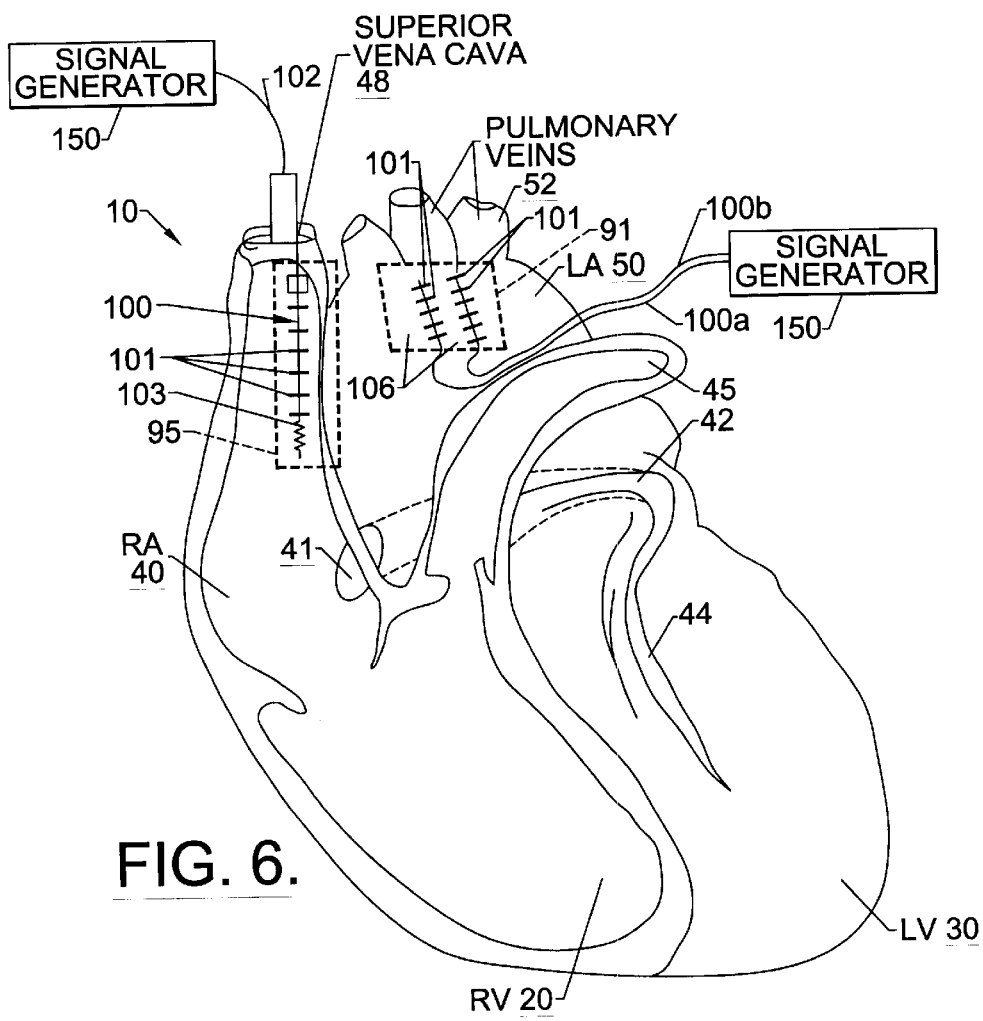
FIG. 6 is a schematic illustration of a human heart illustrating multi-site pacing electrodes in localized regions of the myocardium according to the present invention.

Exemplary localized regions 90 are identified by the broken line windows illustrated in FIGS. 4–6, and 11. For example, in certain embodiments, such as for treating or preventing atrial tacharrhythmias, electrodes (such as line electrodes, as will be discussed further below) may be placed against or proximate the atrial epicardium in the pericardial space or disposed on catheters such that they are held along the right side of the atrial septum or where the atrial septum intersects with the posterior atrial wall in the right atrium. In other embodiments, suitable locations may include positioning the electrode(s) where the refractory period is short and/or where activation occurs rapidly (preferably most rapidly) during the tachyarrhytmia. In certain embodiments, pacing the region of slow activation may be advantageous along with or as an alternative to pacing of the fast region. For example, as shown in FIGS. 4 and 6, a desired localized region 90 in the atria may include a region 91 in the left atrium 50 near the pulmonary veins 52. In other embodiments, one or more of the localized windows 92, 93 shown in FIG. 4 may be suitable for pacing ventricular arrhythmia. Another localized region 93 can be associated with the left ventricle (which in some embodiments, may be the anterior and lateral basal two-thirds of the left ventricle). FIG. 5 illustrates a localized region in the right atrium 40 proximate the SA node 62.

FIG. 6 illustrates two different localized regions, 91, 95 and two different arrangements of electrodes 101. Both embodiments show the electrodes 101 arranged on a line (either 100 or 100a, 100b). The electrodes 101 are operably associated with a signal generator 150. The localized region 91 is shown associated with left atrium 50 in a region near the pulmonary veins 52. The other localized region 95 shown in this FIG. 6 is in the right atrium 40. As shown, a plurality of electrodes 101 are held such that adjacent ones are mounted proximate to and in serial alignment to the others and arranged so that they are electrically in series on a common lead wire 102. One or both of these localized regions may be used to pace the heart according to the present invention. Of course, other regions may be targeted as well as other electrode(s) configurations. For multiple lines, the line electrodes 100a, 100b may be configured to transmit the stimulation synchronously or asynchronously. It is anticipated that using electrode pairs (at two lines of discrete electrodes (FIG. 7) or at least two elongated electrode configurations (FIG. 10)) which are spaced apart a predetermined distance so as to inhibit reentry circuits therebetween may increase the amount of capture area over electrode configurations used alone.

In some embodiments, about 10–80 electrodes 101 may be held on a common lead wire 102, and preferably between about 20–30 electrodes 101. The electrodes 101 may be configured and sized such that they have the same configuration and length (for example, on the order of about 1–5 mm in length and separated from the adjacent electrode(s) by about 0.5–10 mm). In certain embodiments, each electrode 101 is separated by a gap of about 1–5 mm from the next adjacent electrode 101. The line electrode 100 may be configured such that each electrode 101 thereon delivers substantially the same stimuli to the adjacent tissue (the pacing train can be delivered such that each electrode stimulation site is exposed substantially simultaneously or concurrently to the same stimulation pulse strength).

Figure 7:
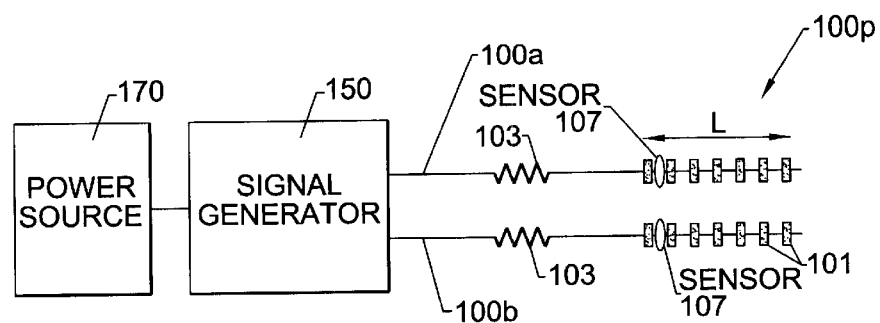
FIG. 7 is a schematic illustration of a pacing system according to one embodiment of the present invention.

In order to regulate or decrease the edge effect of the stimulation pulse transmitted to the patient across the multiple sites (where increased current may be found at edges distal, proximate or sharp regions of the electrode body or line), the stimulation pulse line or electrodes can be configured with increased resistivity. As shown in FIG. 7, in certain embodiments, at least one resistor 103 can be mounted to the lead wire 102 so that the electrical current associated with the pacing train pulses delivered through the line electrode 100 is distributed more evenly therealong (in certain embodiments this may include configuring the electrode or electrical communication such that the current or pacing shock is substantially the same at each electrode 101. As shown in FIG. 7, a first resistor 103 is located between the electrode(s) 101 and the pulse generator or signal generator 150. In position, the electrical signal of the stimulation pulse travels over a path initiating at the generator to the line or lead, to the resistor, and to the electrode to the heart. Thus, for a stimulation input from the signal generator 150 to the line electrode of about 30 mA, and for a line electrode 100 having about 24 electrodes thereon, an average of about 1.25 mA can be output from each electrode 101. Suitable commercially available line electrodes may include defibrillation electrodes well known to those of skill in the art. In some embodiments, the defibrillation electrodes which are adapted to reside in the heart in the vein(s) of a subject may be particularly suitable. See also, U.S. Pat. Nos. 5,107,834, 5,224,476, 5,978,704, and 6,002,962, the contents of which are hereby incorporated by reference as if recited in full herein.

In certain embodiments, the pacing electrode(s) is configured to have a resistivity which is substantially equal to or above that of the myocardium tissue. The pacing electrode(s) may be configured with a resistivity value which is about 100 $\Omega$/cm or greater, and in some embodiments the resistivity may be about 300 $\Omega$/cm or greater. This increased resistivity may be provided in a number of suitable ways, such as by including an alloy in the metallic conductive electrode material to increase the resistance of conductive electrodes, using conductive ceramic or increased resistivity materials (over conventional highly conductive metallic electrodes), and using a higher resistance backing material disposed over the inner surface of the electrode (away from the side that contacts the tissue).

Figure 9A:
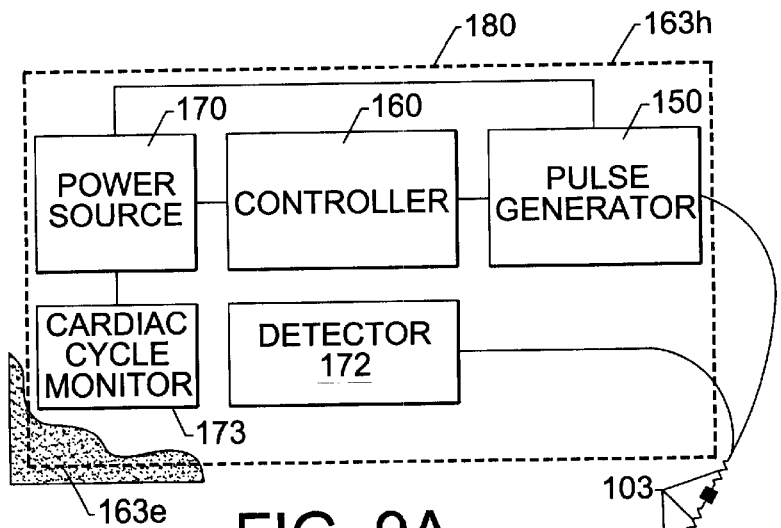
FIG. 9A is a schematic illustration of a pacing system according to another embodiment of the present invention.
Figure 9B:
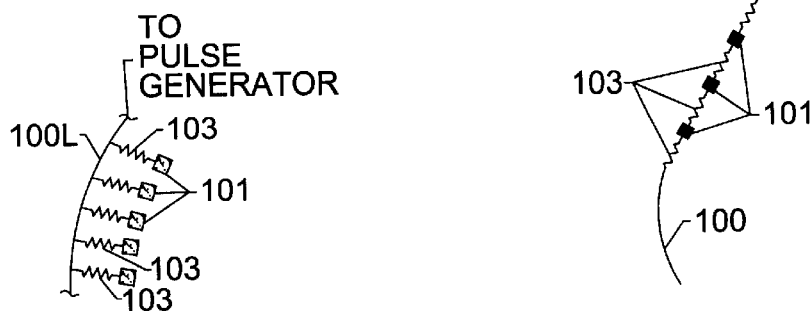
FIG. 9B is a schematic partial illustration of an alternate electrode arrangement with increased resistivity according to embodiments of the present invention.

As shown in FIG. 9A, a plurality of resistors 103 are spaced in series about the plurality of electrodes 101 (positioned electrically between the electrode and the line connecting the pulse generator 150). The plurality of resistors 103 may be configured so as to position a resistor between each adjacent electrode or at selected intervals along the length of the line 100 or catheter. FIG. 9B illustrates that the resistance 103 and electrodes 101 may be arranged electrically in parallel off a central line 100L. Other arrangements may be used as suitable. The resistor may be provided by a resistive element (an electrical component), or by a material, wire, electrical connection or other suitable technique selected to provide the desired operational resistance. For certain embodiments, such as for example, contiguous body electrodes (or line electrodes) or discrete electrodes, a resistive backing material may be applied to the inner wall of the electrode (at selected regions or along the entire length thereof) to increase the electrical resistance across which the stimulation pulse is transmitted. That is, the backing material can be interposed in the electrical path such that the signal travels from the signal generator down the lead wire to the backing material and then to the electrode(s). Configuring the plurality of electrodes with increased resistance (such that they present a resistance equal to or higher than the myocardium tissue) may also help regulate the shock strength delivered to the plurality of sites along the length of the electrode line (or electrodes).

Figure 10:
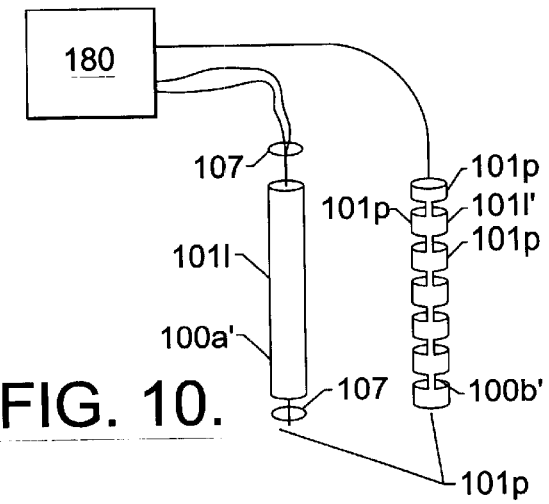
FIG. 10 is a schematic illustration of another embodiment of a pacing system according to the present invention.

As noted above, in some embodiments, in lieu of, or in addition to, a plurality of discrete point or line electrodes, a contiguous length electrode 1011 can be used, as shown for example in FIG. 10. As also shown in FIG. 10, in some embodiments, a contiguous length line electrode 1011' may be configured to provide discrete contact points 101p along its length. The discrete contact points 101p can provide multi-site contact points and stimulus similar to the line electrode configurations described above. The discrete contact points 101p may be provided by removing material to provide gap spaces therealong, by coating or forming alternating regions with a non-conductive material, and the like. In certain embodiments, the contiguous length electrode bodies can have lengths of from about 0.25 cm to 15 cm, and preferably from about 1–5 cm. The conductive regions can be a continuous body or separated by gap spaces of from about 0.5–10 mm or lesser or larger distances.

In certain embodiments, the electrodes 101 are operably associated with a signal generator 150 and a power source 170 which, during operation, supplies the electrical stimulation pacing train signals to the desired sites of the myocardium. Line, point, or contiguous or discontinuous body electrodes can be positioned and held in desired locations proximate the myocardium in a number of ways. For example, point electrodes can be sized such that they can be injected into position with the use of a minimally invasive tool (such as a trochar or other tool) which can enter the cardiac region through the chest wall and deposit the electrode(s) 101 at the myocardium (within the pericardial space) without requiring open-heart surgery. Of course, catheters can be used to hold point or line electrodes in a desired arrangement or to position them in location within the lumens of the heart proximate desired myocardium regions. For example, in some embodiments, as noted above and as shown in FIG. 11, the system 180 can include one or more catheters 190 which are insertable into the heart (typically through the superior or inferior vena cava) without the need for surgical incision into the heart. The term "catheter" as used herein includes "stylet". The term "lead" indicates at least one electrical line extends to the electrode. The catheter may hold electrodes and leads or the lead with its associated electrode(s) may be used independently of a catheter, depending on the application/resident position.

In certain embodiments, each of the catheters 190 can hold one or a plurality of stimulation electrodes 101 thereon, the electrodes 101 can be electrically connected in series, as for the line electrodes 100 discussed above, or the electrodes 101 can be provided as point electrodes each separately connected to the signal generator 150. Thus, the catheter 190 contains at least one lead wire (at least one common line for line electrode (electrically serially connected) configurations and a plurality for point electrode configurations). The catheter 190 may include additional sensors 107 therealong for sensing one or more of the onset of a treatment condition or the intrinsic cardiac cycle. See U.S. Pat. No. 5,978,704, entitled, Method and Apparatus for Treating Cardiac Arrhythmia, the contents of which are hereby incorporated by reference as if recited in full herein.

In certain embodiments, one or more sensing electrodes (which may also be a stimulus electrode) positioned proximate the pacing region/site can be used to determine desired pacing parameters, such as, but not limited to, to determine the desired stimulation signals (intensity, duration of the pulse or train, rate, and the like) and if the pacing is effective (such as by measuring the captured area or regularity of the intrinsic cycle).

Figure 8:
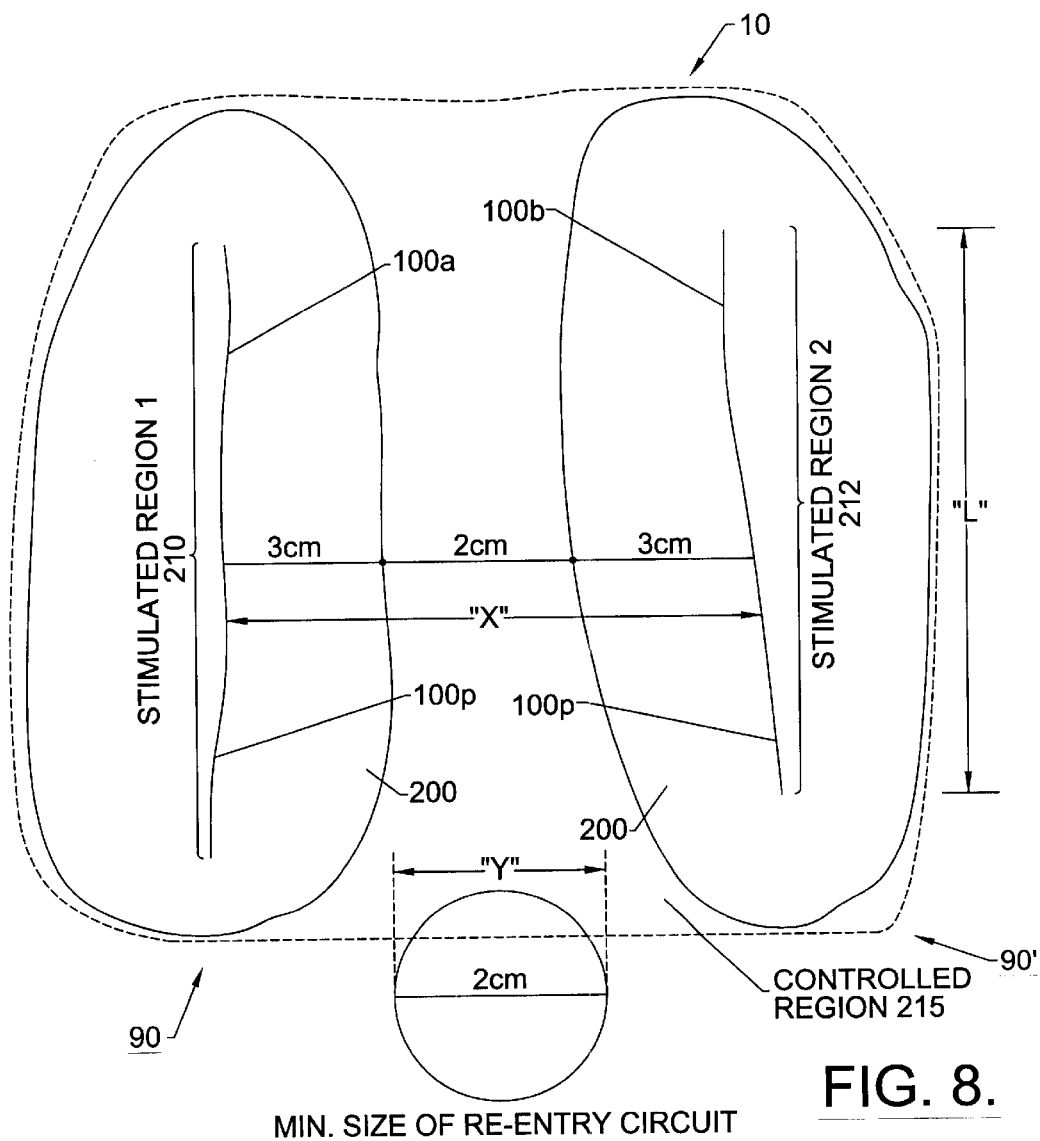
FIG. 8 is a schematic illustration of an electrode pair located in proximate localized regions of the myocardium according to one embodiment of the present invention.

In some embodiments, line electrodes 100a, 100b can be arranged as an operable pair 101p such as shown in FIGS. 6, 8, and 10. That is, each of the line electrodes 100a, 100b (or in other embodiments, corresponding points or elongated contiguous electrodes) may be operably associated so that they can substantially simultaneously stimulate their respective (but spaced apart) regions about a targeted portion of the myocardium (as noted above the pair may also be operated asynchronously). Pacing from electrode pairs 100a, 100b may be particularly effective at capturing and reducing (potentially even eliminating) the number of reentrant circuits in the myocardium. That is, because fibrillation may be maintained by reentry paths which typically require a certain operative size, the multi-site or localized region pacing electrode configuration can be spaced to be less than the size needed to allow reentry, thereby inhibiting reentry, and, thus, controlling or stopping the fibrillation event. Indeed, employing two or more electrode configurations in a spaced relationship sized to correspond to be less than an area capable of supporting reentry may provide an increased capture area over the capture area for two individual electrodes not arranged to be so spatially related when summed together (the sum of the whole being greater than the parts).

In certain embodiments, as shown in FIG. 8, for line electrodes 100a, 100b which are spaced apart a desired distance "X", typically of about 2–8 cm( shown as 3 cm) on each side of a center line associated with the line electrode 100, reentrant circuits may be reduced in a captured portion of the myocardium 200 (the captured portion is illustrated by the shaded area in the figure) which extends beyond the length of the directly stimulated regions 210, 212. The distance "X" is selected to be on the order of or less than that needed to support a reentry circuit, shown as "Y" in FIG. 8. Thus, placing two line electrodes 100a, 100b in parallel and spaced apart a distance "X" in the same localized region 90 or within proximate localized regions 90, 90' less than distance "Y" (shown as spaced apart about 6 cm) may inhibit or even prevent reentry and maintenance of tachyarrhythmia in the region between the two line electrodes 100a, 100b. FIG. 10 illustrates the electrode pair 101p as including at least two contiguous body elongated line electrodes 1011, 1011' which are configured with a length which occupies or covers a larger stimulation area over conventional single point pacing systems. In certain embodiments, the length may be, but is not limited to, between about 0.25–15 cm, 1–10 cm, or 2–5 cm.

In other embodiments, as is also shown in FIG. 8, which may be particularly suitable for reentrant circuits generally having about a 2 cm minimum size, the line electrodes 100a, 100b or electrode pairs 101p may be spaced such that they are about 8 cm apart (in some embodiments this places them within one localized region 90 or within two proximate, localized regions 90, 90') and are able to substantially reduce or eliminate reentry between the two lines of electrodes 100a, 100b. Thus, the electrode pair 100p, properly positioned in the subject, can provide a captured or controlled region 215 which encompasses the length of each line electrode (plus about 3 cm in each direction) and about 3 cm beyond the centerline of each. The electrode pair 100p also can capture the 2 cm between the two lines to provide a captured region having a perimeter which has two sides of about 14 cm and the length dependent on the length of the line electrode stimulation. In certain embodiments, the electrode pairs 100p are configured to provide a captured region which is above 40 mm$^2$. In certain embodiments, the captured region may be between about 100–6000 mm$^2$ (or more) for at least two line electrodes (or electrode pair). For example, in the ventricles, for two spaced apart line electrodes, the capture region may include the region between the electrode pair (estimated at approximately half the area captured by a single electrode (which can typically be at least about 40 mm ) as well as adjacent regions extending away from the other opposing line electrode.

Figure 11:
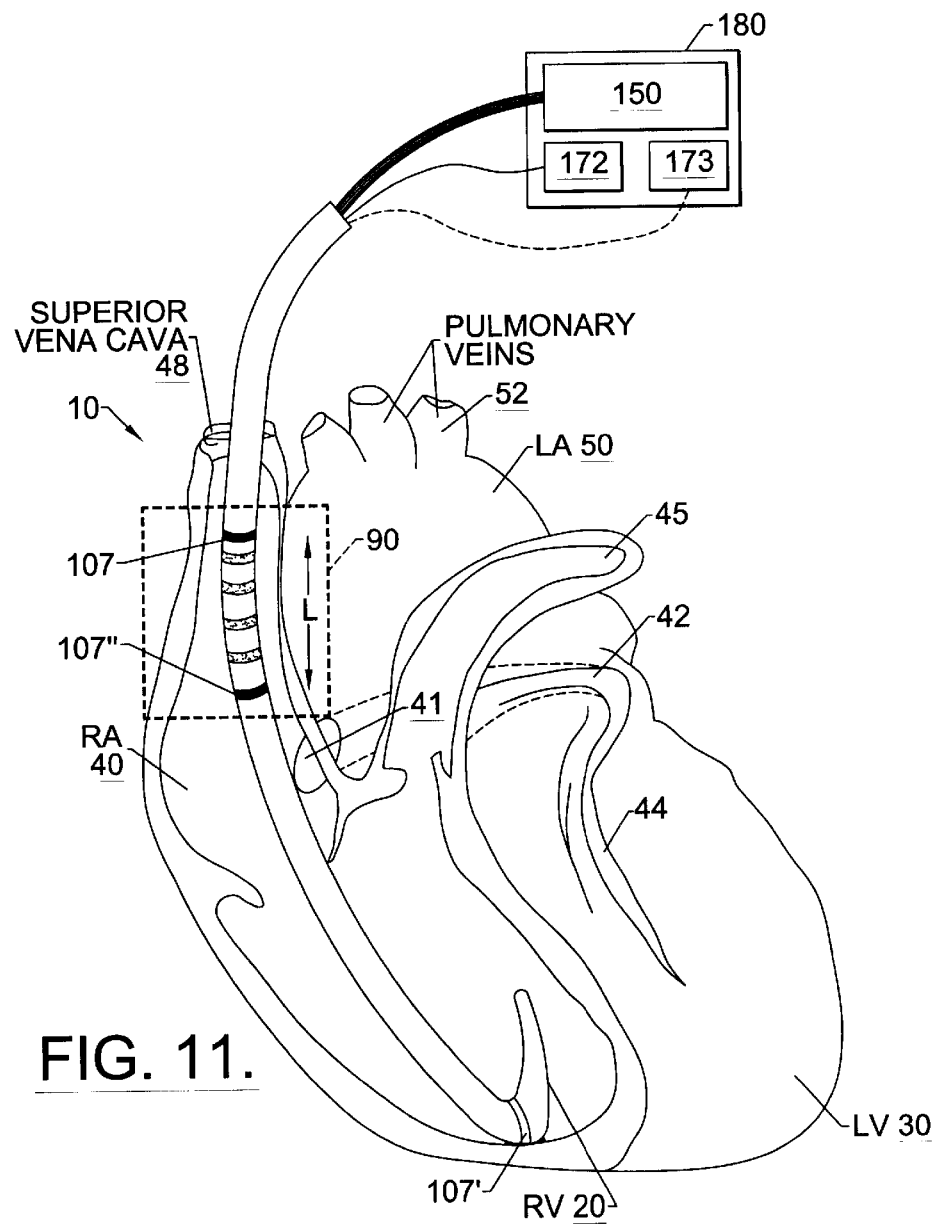
FIG. 11 is a schematic illustration of another embodiment of a pacing system according to the present invention.

Referring to FIG. 9A, the pacing system 180 can include the pulse generator 150, the controller 160, the power source 170, a cardiac cycle monitor 173, and a detector 172. The detector 172 can be configured to determine the presence of an irregular condition, such as the onset of arrhythmia or fibrillation. The detector 172 and the cardiac cycle monitor 173 can be operably associated with one or more sensors 107 (or sensor 107' in FIG. 11) which maybe held on one or more of the line electrodes 100a, 100b as shown in FIGS. 7 and 10 or on a catheter 190 as shown in FIG. 11. In other embodiments, the sensor 107 may be separate from the pacing stimuli electrodes 101 altogether. The cardiac monitor sensor 107' and the detector sensor 107 can be a plurality of sensors. In addition, the cardiac monitor sensor 107' and the detector sensor 107 can be the same sensor or different sensors placed in different locations in the subject.

The electronic processing circuitry of the pacing system 180 may be held on an external device (such as a remote housing which holds the operating components therein), or in a biocompatible implantable housing which holds the operating circuitry in a hermetically sealed body. The pacing system 180 can include an electronic circuit which includes one or more amplifiers (not shown) for amplifying sensed cardiac signals. As such, the detector 172 may analyze the amplified signals to detect the onset or presence of an atrial and ventricular arrhythmia or fibrillation condition and to identify when or if ventricular fibrillation (or other arrhythmia, depending on the specific treatment for which the device is configured) is present. The detector 172 may be one of several known to those skilled in the art. In operation, the sensors 107, 107' proximate one or more regions in the heart can provide a sensing signal into the pacing system 180. Other suitable regions were discussed above and can also include, for example, one or more of the basal and apical LV free wall, RV free wall, and the RV side of the interventricular septum. It will also be appreciated by those of skill in the art that the sensing electrodes 107 may also be a plurality of sensing electrodes adapted to transmit a plurality of signals that are positioned in cardiac areas, such as, for example, the CS, suitable for detecting the irregular condition, as is known in the art. In certain embodiments, the sensing electrode(s) can be the same as the pacing electrode(s). This may help establish a more reliable activation rate and/or to detect other parameters of the desired or targeted region, as the pacing and sensing are formed from the same electrode(s).

As noted above, in certain embodiments, the pacing system 180 can also include a cardiac cycle monitor 173 ("synchronization monitor") for providing synchronization information to the controller 160 (which in certain embodiments may be helpful for pacing). The synchronization is typically provided by sensing cardiac activity, but may also include other sensing electrodes. To control pacing, one or more sensing electrodes can be positioned proximate the pacing electrode. For a line electrode, this may be at a proximal or distal end portion, or extend about a more central portion (such as through one of the gap spaces in a discontinuous body elongated electrode). The pacing electrode may also be the sensing electrode in some embodiments.

In some embodiments (as will be discussed further below), the present invention can provide pacing stimulation in conjunction with a defibrillation shock pulse or pulses. As such, the synchronization monitor 173 can be used to time an atrial defibrillation shock pulse to provide additional assurance that defibrillation shock pulses are not delivered during sensitive portions of the cardiac cycle so as to reduce the possibility of inducing ventricular fibrillation. Ventricular sensing for timing the shocks for atrial defibrillation may be performed from the RV and/or LV electrodes used as in defibrillation devices known to those of skill in the art. See U.S. Pat. No. 5,978,704, the contents of which were incorporated by reference hereinabove. The defibrillation shock may be delivered proximate in time to the pacing stimulation (before, during, or after).

Generally stated, in certain embodiments (for defibrillation shocks), upon a signal from the detector 172, the controller 160 signals a capacitor charging circuit (not shown) which then charges the storage capacitor (not shown) to a predetermined voltage, typically from a battery source 170. In some embodiments, the storage capacitor can be about 20 to 400 microfarads in size, and may be a single capacitor or a capacitor network (further separate pulses can be driven by the same or different capacitors). The discharge of the capacitor is controlled by the controller 160 and/or a discharge circuit (not shown). The controller 160, based on information from the detector 172 for the pacing signals and/or the synchronization monitor 173, typically allows or directs the pacing trains to be relayed to either a discharge circuit for further processing (i.e., to further shape the waveform signal, time the pulse, etc.) or directly to a switch and output to the electrodes 101. The controller 160 may also control the proper selection of the pacing or defibrillation pulses and associated electrodes to direct the switch to electrically activate the desired electrodes. As an alternative to a detector, the defibrillation pulses may be triggered by an external signal administered by a physician, with the physician monitoring the patient for the appropriate time of administration.

Numerous configurations of pulse generators 150 and controllers 160 may be employed as is well known to those of skill in the art. For example, the pulse generator 150 may include a single capacitor, and the controller 160 may be configured so that the defibrillation shock pulses are generated by discharge of the single capacitor over a controlled discharge time. For pacing shocks, the pacing may be powered directly off a power supply, such as a battery, without requiring a capacitor.

The pulse generator 150 may include a first and second capacitor, with the controller 160 configured so that the first and second series of pulses is generated by the discharge of the first capacitor and the third (and any subsequent) train pulses (particularly defibrillation pulses) can be generated by the discharge of the second capacitor. In still other embodiments, the pulse generator 150 can include a first and second capacitor, and the controller 160 may be configured so that the pacing train pulses are generated to the electrodes directly from the battery and any defibrillation pulse is generated by the discharge of the first and second capacitors.

It will be appreciated by those of skill in the art that the pulse generator 150 can include a power supply and any number of pulse shaping circuits (which may include a single capacitor or a bank of parallel capacitors sufficiently charged and sized to be able to provide the stimulation pulses and/or defibrillation pulses as desired) which are configured to deliver the stimuli to predetermined electrodes positioned in the heart. Additionally, the pulse generator 150 can include two or more separately charged capacitors (or bank of parallel capacitors) on separate lines to provide two separate and sequential shock pulses as controlled by the controller 160 and/or the discharge circuit. In certain embodiments, the pulse generator 150 can include a relatively large capacitor for insuring sufficient charge and decay period (i.e., long time constant and low tilt) to provide sufficient energy for a plurality of pacing train stimuli (such as two or three or more serially delivered train stimuli). For example, a capacitor with capacitance in the range of 200–1000 µf or more, having an associated time constant in the range of 30 ms, would typically be charged to approximately 100–200 volts and would deliver a desired V(peak). In the alternative, wherein the electronic package employs a circuit to further shape the waveform, the capacitor may be charged to a higher voltage range (such as around 200 V or more).

In operation, the controller 160 can deliver (substantially simultaneously) a preselected electrical pulse to the multi-site electrodes 101 (discrete electrodes, line electrode, or electrode pairs 101p) through a switch which is preferably programmable. The pulse generator 150 can include a discharge circuit and switch. Therefore, it will be appreciated that in operation, in response to an input from the detector 172, the controller 160 controls the pulse generator 150 to deliver the pacing train stimuli to the proper electrodes 101 (pairs 100, 100p). The controller 160 may also consider information or data input from the cardiac cycle monitor 173 to synchronize the timing of pacing stimulation in accordance with the cardiac cycle information received from the synchronization monitor 173. Alternatively, or in addition thereto, the sensing electrode can also be configured to detect the onset of a fibrillating event and/or to monitor or sense during the pacing protocol for effectiveness of the pacing treatment.

The pacing system 180 can also include a receiver/transmitter coupled to the internal controller 160 for communicating with an external controller (not shown). Thus, the pulse regimen can be altered by external input to the controller 160 to alter, for example, the waveform, the voltage, the electrode coupling, or even to retrieve data monitoring data received and stored in memory about the number of atrial arrhythmia events or fibrillation episodes and the effectiveness of the shock level.

Figure 12:
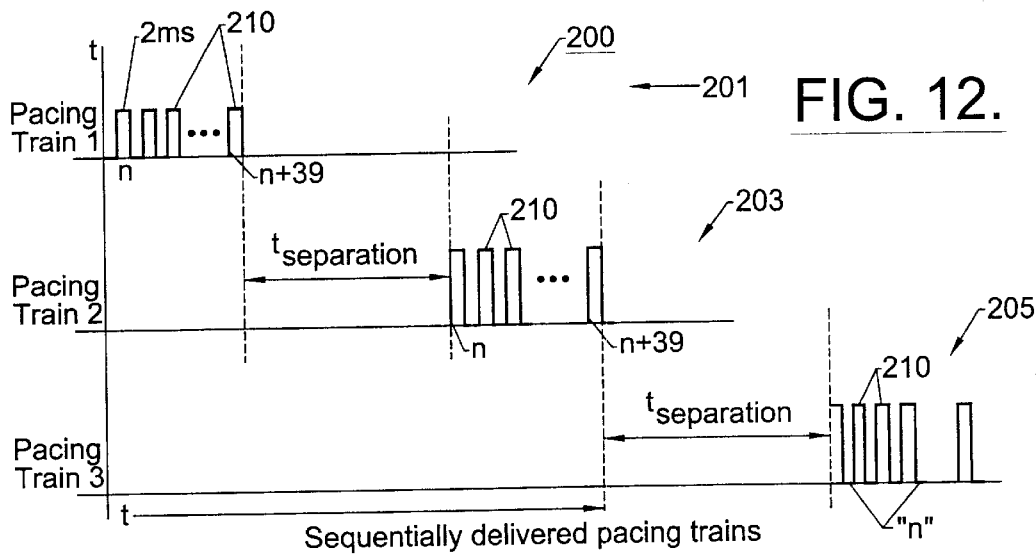
FIG. 12 is a graph of a sequentially delivered plurality of pacing trains according to an embodiment of the present invention.

Turning now to FIG. 12, embodiments of the pacing train stimuli according to the present invention will be described. The pacing stimuli can be fixed (pre-determined) or reactive to sensed in situ conditions at the time of activation. Certain embodiments of the present invention comprise generating and transmitting at least one, and typically, a plurality of sequentially transmitted pacing train stimuli to multiple sites in a localized region of the heart. Thus, one, two, three, or more pacing trains 200 (each having a plurality of stimulation pulses 210) can be used. FIG. 12 illustrates a series of three sequentially delivered pacing trains 201, 203, 205. Each of the pacing trains 201, 203, 205 can be separated by an interval of time (shown as $t_{separation}$ in the figure). The $t_{separation}$ may last from 3–15 cycle lengths, which generally corresponds to about 300–200 ms (activation cycle lengths are generally longer than about 100 ms). The interval between the actual pulses can be established based on a median or mean measured value of the length established over 3–15 cycles. Thus, the pulse interval can vary, and may be re-established during pacing (to include the more proximate cycle times and perhaps discard the earlier cycle times). As such, the activation interval may be described as a percent of the intrinsic interval and, in certain embodiments, that range will typically be on the order of about 75–115% of the intrinsic interval (the intrinsic cycle length) or about 75–200 ms, depending on the species and the associated intrinsic rate of the heart.

In certain of the embodiments, the activation of each pacing train 200 (or the delay between) can be established based on the number of intrinsic activation intervals after the onset of the condition. Thus, the first pacing train can be delivered after the intrinsic cycle length has substantially elapsed (such as after about 75–115% of the intrinsic cycle length has elapsed after the between about 3–15 (such as the twelfth) detected intrinsic activation). Therefore, the first delivery time and the interstimulus intervals can be based on an in situ determined intrinsic cycle length. This cycle length can be monitored and the time for the number of intervals used to calculate a new median or average activation interval for timing/determining the next pacing train. As is known to those of skill in the art, the cycle length is the time between two consecutive activations in a region of the heart, or the entire heart, during any rhythm.

In some embodiments, the pacing system 180 is configured to sense from at least one in situ sensor positioned in the heart to identify the intrinsic activation rate of the heart of the subject. The intrinsic rate can be electronically determined by the localized sensor 107, the synchronization sensor 107', or a different sensor, as desired. The intrinsic rate is monitored by the controller 160 of the pacing system 180. The pacing trains 200 can be transmitted based on or responsive to information obtained regarding the identified intrinsic rate. In addition, the intrinsic rate can be monitored. Further, the pacing trains 200 may be delivered based on the heartbeat of the subject (such as after 10 beats from the start or finish of the preceding pacing train). Each of the pacing trains 200 provides a plurality of stimulation pulses to each of the desired electrodes 101 in the targeted localized region 90. The pulses are shown as a series of square waves. Other waveforms can also be used, such as monophasic and/or biphasic, sinusoidal, ramped, exponentially decaying, and the like. In addition, the type and operational polarity of the electrodes may vary, and can include one or more of unipolar anodal, unipolar cathodal, and bipolar configurations.

The individual pulses 210 can have a duration or length between about 0.25–20 ms, and preferably are from about 1–6, and more preferably about 1–3 ms. For embodiments employing a plurality of pacing trains, each of the pacing trains 200 can be the same (current strength, pacing rate, and pulse shape) or each of the pacing train stimuli can vary. Further, each of the individual pulse stimulus 210 within the pacing train 200 may also vary and need not be the same throughout the entire length of the pacing train. In certain embodiments, the signal shape or strength may vary from the first to the second or the third pacing trains 201, 203, 205. For example, the first pacing train 201 may have a lesser electrical strength than the other two pacing trains 203, 205. In certain embodiments, the number of pulses ("n") can be between about 3–120, and in certain embodiments between about 10–60, or 30–60 pulses. In other embodiments, such as for atrial fibrillation applications, longer pulse trains (longer periods of fibrillation and longer periods of pacing) may be desired. Further, longer periods (longer pulses in the pacing trains) may increase the likelihood of successful capture and/or may increase the size of the area of capture.

The pacing trains 200 are typically configured to fit within a treatment window and delivered so as to inhibit damage to the heart. Thus, each of sequentially delivered pacing trains 200 can vary in length slightly from the others, but have average cycle lengths in the range of between about 80–350 ms, depending on the species and intrinsic rate. For certain embodiments, the first pacing train 201 can be transmitted within about 4–6 seconds after the onset of the irregular condition (such as fibrillation); the second pacing train 203 can be transmitted within about 9–20 seconds after the onset, and the third within about 15–30 seconds after the onset. For ventricular fibrillation, the time between pacing and onset of the fibrillation can be very important as ventricular fibrillation can be rapidly fatal. For atrial fibrillation, the time between the onset of the arrhythmia and the delivery of the pacing train may be delayed for minutes or even hours. For atrial fibrillation treatment, it is preferred that pacing be delivered in a timely manner so as to inhibit the development of thrombi that may embolize with defibrillation. It is noted that greater or lesser numbers of pacing trains can be used and that different intervals may also be used.

In certain embodiments, the current strength of the pacing trains 200 is set at a multiple above the diastolic pacing threshold ("DPT"). Preferably, the current strength is set at about 5–15 times the DPT. DPT can be described as the lowest current level which initiates electrical activation of the tissue during diastole. For the current used to stimulate the line electrode configurations, a lowest current value which initiates activation along substantially the entire line can be used as the value associated with the DPT. The DPT value may vary for the type of electrode and electrode configurations employed as well as for the tissue or region selected for pacing and, even, patient-to-patient as the physiology of the heart also varies. In certain embodiments, at least some of the pacing trains are set to provide stimulation pulses having a strength which is at about 5–10 times the DPT value, and more preferably at a stimulation current which is about 8–10 times, and even more preferably at about 10 times that of the DPT.

The DPT of the localized region can be determined in situ by a corresponding sensor(s) positioned in the myocardium in the localized region as shown, for example, in FIG. 11. The DPT can be determined with a pacing algorithm that identifies the lowest strength a stimuli of a certain waveform and duration is in order to stimulate the tissue at least about 50% of the time. The sensor(s) may also be used to determine which waveforms are more responsive for the particular subject and/or to determine if a stimulus delivered by the same or a different electrode successfully captures the myocardium. It is anticipated that, because the electrode(s) will lie differently in each patient, it may be desirable to determine the DPT at the time of implantation, and possibly post-implantation at desired intervals. Post-implantation assessment may allow the stimuli to be altered to be more effective for chronic use. In other embodiments, conventional pacemakers with "autocapture" capability can be used to automatically determine the threshold value, and this base value can be used to provide the 5–10 × multiplier for pacing. As noted above, the localized region can be sensed (with one or more sensing electrodes) during pacing (the data being relayed back to the controller) to adjust or set one or more of: (a) the stimulus amplitude; (b) the duration of the pacing stimulation treatment; and (c) the pacing rate. The pacing system may also detect when to terminate the stimulation or how effective the pacing stimulation has been at capturing the tissue.

The DPT sensor 107" can be used to calibrate or adjust the pacing system 180 as an initial part of operational set-up (and adjusted over time as appropriate) and/or to monitor the DPT at various times (continuously or semi-continuously) to help establish the intrinsic rate of the subject. Thus, an appropriate stimulation (DPT) value can be set by employing a sensor 107" (which can be the same as the sensors 107, 107" noted above) to detect when tissue is successfully stimulated as electrical current is incrementally input to the heart at a position which is proximate to the localized region and/or electrodes 101.

In other embodiments, operational strength of the system 180 can be preset based on a statistical probability of the DPT value as measured across a plurality of patients (with a certain safety factor added thereto). Alternatively, pacing system 180 can include a sensing algorithm which can automatically calibrate and adjust the stimulation pulse strength upon installation in the patient (such as stepped in 0.1 mA increments based on the patient's sensitivity thereto).

In some embodiments, it may be desirable to administer pharmacological agents to help increase the degree of organization so that pacing can capture larger regions of the heart (and help reduce the number of reentrant circuits).

The present invention may combine treatments such as by providing pacing train stimuli during fibrillation and then delivering one or more defibrillation shock pulses to multiple sites within one or more targeted localized regions (through a plurality of discrete electrodes, a line electrode, or a contiguous or discontinuous surface body electrode. In certain embodiments this may be accomplished by positioning the electrode(s) in a localized pacing region(s) of the myocardium where the defibrillation shock would have a relatively weak effect. Thus, if pacing can control activation in this region so that it stops with termination of the pacing stimulation, then the defibrillation shock can be decreased to a strength sufficient to halt fibrillation in the remaining portions of the myocardium not captured by the pacing. In certain embodiments, the defibrillation shocks may be synchronized with the pacing stimulation so that the defibrillation shock is inhibited from reinducing fibrillation in the region captured by pacing. This combination treatment may be particularly suitable for atrial fibrillation where there is often patient discomfort associated with using strong shocks.

Thus, for embodiments where the pacing system 180 is also configured to deliver one or more defibrillation pulses, it is anticipated that the defibrillation pulse be delivered after the pacing train stimuli and that a lower energy defibrillation pulse be used over conventional defibrillation treatments. In certain embodiments, for atrial defibrillation pulses, the energy of the atrial defibrillation pulse is less than about 8 joules, and is preferably not greater than 6 joules, still more preferably not greater than 4 joules, and most preferably not greater than 2 joules. The energy of the second atrial defibrillation pulse (when desired) can be similar to and is typically not greater than the energy of the first defibrillation pulse (although such a result is possible where a dual capacitor design is employed), and is preferably not greater than 8 joules, more preferably not greater than 6 joules, still more preferably not greater than 4 joules, and most preferably not greater than 2 joules. The second atrial defibrillation pulse can follow the first atrial defibrillation pulse by 0 to 500 milliseconds, and more preferably follows the first atrial defibrillation pulse by 0 to 200 milliseconds. In the alternative, the second atrial defibrillation pulse may overlap the first atrial defibrillation pulse, for example, by from one-fourth to three-fourths of the total shock duration (the duration of both shocks in series). The duration of each shock may be, for example, from three to twenty milliseconds, with total shock duration being, for example, from four and one-half to forty milliseconds.

In certain embodiments, particularly where the pacing system 180 also delivers defibrillation shocks, the housing can be configured with an active external portion 163e (FIG. 9A) of the housing, with the housing 163h preferably implanted in the left thoracic region of the patient (e.g., subcutaneously, in the left pectoral region) in accordance with known techniques as described in U.S. Pat. No. 5,292, 338, the contents of which are hereby incorporated by reference as if recited in full herein.

The invention will now be illustrated with reference to certain examples which are included herein for the purposes of illustration only, and which are not intended to be limiting of the invention.

EXAMPLES

Recent studies have shown pacing atrial and ventricular fibrillation (VF) to be possible. The studies presented herein were intended to determine which parameters influence the efficacy of a pacing train to capture fibrillating ventricular myocardium. Electrode type, current strength, order of the pacing trains, polarity, and VF morphology preceding the pacing trains were investigated.

Methods and Results

A 504 electrode recording plaque sutured to the (right ventricle) RV of pig hearts was used to record the activations of VF and those resulting from the pacing stimulation. Capture of VF by pacing was determined by observing an animated display of the first temporal derivative of the electrograms. A series of electrodes in a line captured the heart more frequently during VF than did a point electrode. Increasing the current strength to 10×diastolic pacing threshold increased the incidence of capture, but increasing this strength further did not. The second or third train of forty stimuli had greater capture rates than did the first train during the same VF episode. Anodal and cathodal unipolar, and bipolar stimulation were equally efficacious in capturing VF. VF activation during the one-second interval preceding pacing was more organized for pacing trains that captured than those that did not. The highest incidence of capture, 46–61% of pacing trains, occurred with a line of electrodes at 10×diastolic pacing threshold delivered by the second or third train.

Materials and Methods

Eight pigs of either gender were studied. Four animals (Group 1) were used to determine if a line of electrodes is more effective at capturing fibrillating myocardium than a single point electrode and if the relative strength of the stimulus or the order of the pacing trains affect the likelihood of capture. The other four animals (Group 2) were used to determine if one pacing modality is more effective at capturing the other modalities, whether VF organization affects capture rates, and whether order of the pacing trains affects the likelihood of capture.

Animal Preparation

The following was performed on both groups of animals. All pre-operative and operative care complied with Section 6 of the Animal Welfare Act of 1989, and adhered to the guiding principles outlined in NIH publication #85-23. Anesthesia was induced with telazol (4.4 mg/kg), xylazine (2.2 mg/kg), atropine (0.04 mg/kg) IM and maintained with isoflurane in 100%. Paralysis was achieved with succinyl choline. The pigs were restrained dorsally recumbent, intubated, and mechanically ventilated. A surface ECG, a femoral arterial blood pressure (ABP), and temperature were monitored. Arterial blood pressure, blood gases, temperature, and pH were monitored and maintained within physiologic ranges.

Figure 13A:
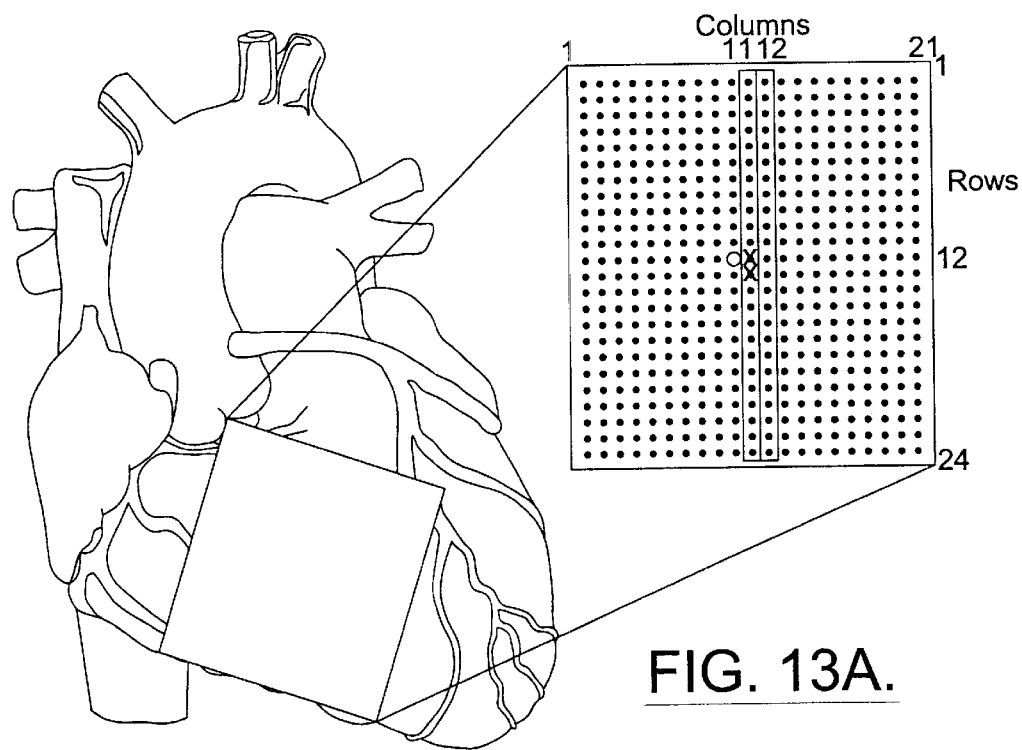
FIG. 13A is a schematic illustration of the experimental preparation of the heart of a subject using a grid of electrodes positioned on the right ventricular epicardial surface extending slightly over the LAD onto the LV.

Following a median sternotomy, an epicardial recording plaque with 504 recording electrodes was sutured over the lateral surface of the right ventricle (RV), with the left anterior descending artery passing beneath the lower portion of the plaque (FIG. 13A). VF was induced by applying AC current for one second to the RV free wall. Rescue shocks were delivered via a transvenous coiled superior vena cava lead electrode and a patch electrode on the LV apex after approximately 25 seconds of VF. A 4 minute or longer recovery period elapsed between each VF episode to allow normal blood pressure and ECG to return.

Experimental Procedure

Figure 13B:
FIG. 13B is a graph of the experimental pacing train used in the experimental set-up of FIG. 13A.

Pacing protocols were performed prior to any VF episodes for each group. The following VF pacing protocol was thereafter performed in both animal groups. Five seconds of VF elapsed before pacing was initiated, during approximately the last 1.5 seconds of which a Macintosh computer (Apple Corp., Cupertino, Calif.) controlled stimulator/recorder detected 11 consecutive activation intervals based on a dV/dt≦−0.5 V/sec recorded from a plaque electrode 2 mm from the pacing electrode (open electrode in FIG. 13 B) in real time. See Rollins et al., Macintosh based programmable cardiac stimulator, J. Am. Coll. Cardiol. 1990; 15:261A (Abstract). The median of the eleven intervals was calculated to represent the intrinsic VF activation rate. Three trains of 40 pulses were delivered per VF episode, with the trains separated by the time taken to acquire the next 11 VF intervals for the subsequent train, approximately 1.5 seconds (FIG. 13B). Based on the results of KenKnight et al., the interval between the last intrinsic VF activation and the first pacing stimulus of the train and the interstimulus interval of the pacing train were set to 98% of the median intrinsic VF cycle length. See KenKnight et al., Regional capture of fibrillating ventricular myocardium: Evidence of an excitable gap, Circ. Res. 1995; 77:849–855. The pacing pulses were 2 ms constant current square waves. For point stimulation, a pair of plaque electrodes was used. For line stimulation, a column of plaque electrodes were individually connected through a 100 kΩ resistor and joined in parallel to the stimulator to evenly distribute the current across the individual electrodes. A plurality of resistors can also be used (preferably each having a resistance above that of the local tissue), each disposed about the length of the line to help provide higher resistivity and/or a more constant applied shock to the tissue. Other increased resistivity-electrode configurations can also be employed.

Figure 14:
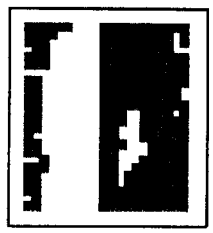
FIG. 14 is a series of screen printouts of an activation front created by overdrive pacing with a line stimulus during normal sinus rhythm. Each snapshot is separated by 5 ms. The black horizontal line represents the line-pacing electrode. The solid black snapshot represents the time of the pacing stimulus. Each pixel is a recording electrode site at which dV/dt was less than −0.5 V/sec during the interval for that frame. Dark gray pixels comprise activation fronts that arose from the pacing electrode.
Figure 14:
Figure 14:
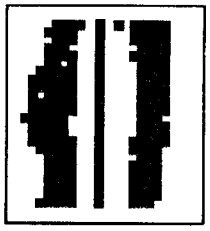
Figure 14:
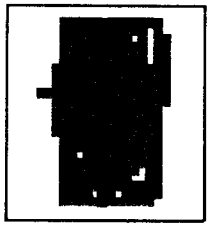
Figure 14:
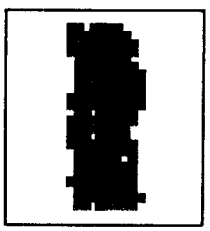
Figure 14:
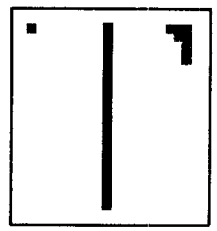
Figure 14:
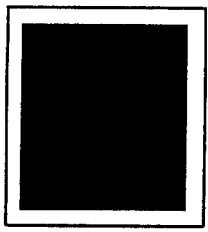
Figure 14:
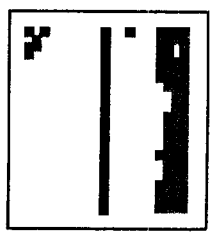

Group 1: The diastolic pacing threshold (DPT) for both line and point stimulation was determined prior to any VF episodes. The bipolar point electrode was two adjacent central plaque recording electrodes, and the bipolar line electrode was two adjacent lines of recording plaque electrodes (FIG. 13A). Point stimulation DPT was determined by increasing current strength from 0.2 mA by 0.2 mA steps until activation was initiated, and then decreasing the strength by 0.1 mA. The DPT was the lowest strength that captured. Line stimulation DPT determination utilized the same technique, except when a stimulus captured, the recordings were animated to determine if the entire line of electrodes initiated the activation front, rather than just segments along the line (FIG. 14). See Laxer et al., The use of computer animation of mapped cardiac potentials in studying electrical conduction properties of arrhythmias. In: Murray A and Arzbaecher R, eds. Proc. Computers in Cardiology, Los Alamitos, Calif.: IEEE Computer Society Press, Piscataway, N.J., 1991, p. 23–26. The lowest current that captured along the entire line was defined as the DPT.

Pacing during VF was performed with bipolar point and line electrodes at 5× and 10×DPT. The strength of the stimuli and electrode configurations (unipolar or bipolar) were randomized. Anode and cathode were reversed after each VF episode to decrease polarization at the electrode-tissue interface. The protocol was repeated until the animal became unstable or six iterations of the protocol were complete.

Group 2: DPTs for 2 ms point unipolar cathode stimulation were determined with an isolation stimulator (World Precision Instruments, New Haven, Conn.) at five locations (electrode numbers 2, 6, 12, 18, and 23) along the line of 24 electrode as described for Group 1. A silver silver-chloride return electrode was sutured to the exposed right sternomastoid muscle.

The VF pacing protocol was similar to group 1. Pacing was performed at 10×diastolic threshold for unipolar anode and cathode, and bipolar stimulation. The two pacing modalities with the lower DPTs were also tested at 10×DPT of the modality with the highest DPT, for a total of five pacing treatments. The stimuli were delivered from either a bipolar line electrode (two adjacent lines of central plaque electrodes), or a unipolar line stimulus (a single line of plaque electrodes, FIG. 13A).

Data Acquisition and Analysis

Unipolar epicardial potentials were recorded from the 504 electrode plaque with a 528-channel mapping system. See Wolf et al., A 528 channel system for the acquisition and display of defibrillation and electrocardiographic potentials, In: Murray A and Arzbaecher R, eds. Proc. Computers in Cardiology. Los Alamitos, Calif.: IEEE Computer Society Press, 1993; p. 125–128. Signals were recorded at a 2 kHz sampling rate with a 500 Hz low pass filter, DC coupling, and a 50×gain. Silver silver-chloride ground electrodes were sutured to the aortic root.

To determine if pacing captured the fibrillating myocardium, the first temporal derivative (5 point) of each electrogram was animated on a 24×21 grid on a computer monitor, representing the 504 plaque electrodes. See Laxer et al., The use of computer animation of mapped cardiac potentials in studying electrical conduction properties of arrhythmias, In: Murray A and Arzbaecher R, eds. Proc. Computers in Cardiology. Los Alamitos, Calif.: IEEE Computer Society Press, Piscataway, N.J., 1991; p. 23–26 Derivatives<−0.5 V/s were allocated a color from light blue (−0.5 V/s) to red (<−1.4 V/s) and considered local activations. Derivatives >−0.5 V/s were dark blue, and not considered local activations. The animations were viewed approximately 40 times slower than real time, enabling the visualization of activation propagation. KenKnight et al. showed that such visualization was a reliable means of determining capture compared to Poincare analysis and Karhunen-Loeve decomposition. See KenKnight et al., Regional capture of fibrillating ventricular myocardium: Evidence of an excitable gap, Circ. Res. 1995;77:849–855.

Figure 15:
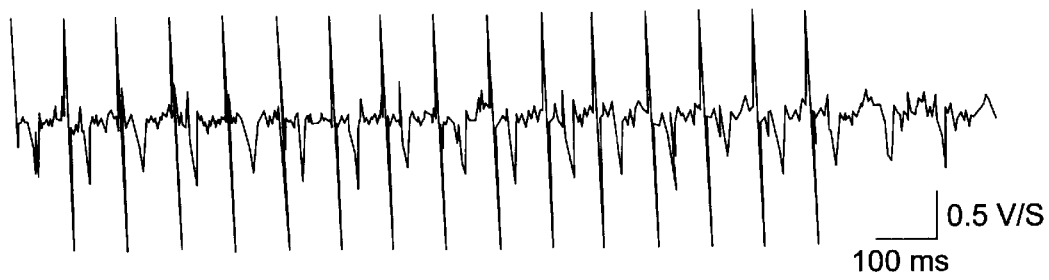
FIG. 15 is a graph of the 5 point first temporal derivative of a unipolar electrogram recorded from a captured region that is phase-locked with cathodal line pacing stimuli. The stimuli were delivered with a coupling interval of 94.5 ms, which represents 98% of the intrinsic preceding VF cycle length. The time-lapse between the stimulus and the local activation is due to the time taken to propagate from the pacing site to the recording electrode, and this time is constant because the time taken to traverse the same distance repeatedly does not change.

A pacing train was considered successful at capturing if it achieved all the following criteria: 1) at least 5 consecutive stimulus-induced activation fronts propagated from the pacing electrode; 2) activations in electrograms from the region deemed captured were phase locked with the pacing stimuli (phase locked: a regular interval on the electrogram between the stimulus-induced artifact and the onset of activation, see FIG. 15); 3) the region beneath the stimulus electrode was not activated immediately prior to delivery of the stimulus; and 4) a minimal region of 40 mm$^2$ (10 recording electrodes) was captured per pacing cycle.

The data from the Group 2 animals were further analyzed with a suite of programs which quantify VF activation patterns. See Rogers et al., A quantitative framework for analyzing epicardial activation patterns during ventricular fibrillation, Ann. Biomed. Eng. 1997; 25: 749–760; Huang et al., Evolution of the organization of epicardial activation patterns during ventricular fibrillation, J. Cardiovasc. Electrophysiol. 1998; 9:1291–1304. To determine if the organization of VF prior to the onset of pacing influences capture efficacy, one second of VF immediately preceding each pacing train was analyzed to determine if differences in the morphology of VF exists for pacing trains that captured versus pacing trains that failed to capture, and among the three trains. The parameters studied were multiplicity, repeatability, the mean area swept out by each VF activation front, the fraction of wavefronts that experienced block within the mapped region, and the percent of activations that resulted from breakthrough from beneath the epicardium. Multiplicity is the number of distinct activation pathways in the VF pattern. Repeatability is the weighted average of the number of wavefronts that propagate over each activation pathway determined in multiplicity. For example, if an activation pattern contains 6 wavefronts equally divided into two pathways, multiplicity would be 2 and repeatability would be 3. All these measures are described in detail elsewhere. See Rogers et al., A quantitative framework for analyzing epicardial activation patterns during ventricular fibrillation, Ann. Biomed. Eng. 1997;25: 749–760; Huang et al., Evolution of the organization of epicardial activation patterns during ventricular fibrillation, J. Cardiovasc. Electrophysiol. 1998; 9:1291–1304.

The effect of the type of pacing electrode, polarity, stimulation strength, and pacing train number on the incidence of capture was evaluated by a repeated measures analysis of variance. Differences in quantitative measures of VF morphology preceding pacing episodes that captured and pacing episodes that did not capture were evaluated by unpaired t-tests. Results are given as mean±standard deviation. P values of <0.05 were considered significant.

RESULTS

Group 1: The pigs weighed 42.9±14.2 kg. The DPT for a bipolar point stimulus was 0.45±0.13 mA, and for a bipolar line stimulus was 9.5±2.5 mA, a mean of 0.40 mA through each of the 24 electrodes in the line. The first train was delivered 4.7±0.6 sec after the onset of VF with a mean cycle length of 114.5±14.5 ms, the second train 10.7±1.1 sec after VF was induced with a mean cycle length of 110.8±13.9 ms, and the third train 16.5±1.6 sec after VF began with a mean cycle length of 109.0±11.6 ms. There was no significant difference between the pacing rates for the three trains.

For pacing initiated during sinus rhythm, an activation induced by a stimulus propagated away from the electrodes in a smooth line (for line electrode stimulation, FIG. 15) or an ellipse (for point stimulation). This was not necessarily the case during VF for point or line stimulation since part of the area beneath the plaque may have been refractory (FIG. 16 and FIG. 17A) or capture occurred along only part of the line electrode (FIG. 17B). If there was no capture, then no activations would initiate from beneath the electrode (FIG. 17C).

Capture never occurred with the first pacing stimulus, and during the first five stimuli occurred only twice. Capture occurred in 49 of the 285 pacing trains. Once a train captured, it was maintained until the train ended in 27 of the 49 trains. When capture was not maintained until the end, it was because the VF activation rate increased and VF activation fronts entered the region beneath the electrode before a stimulus was delivered, thus ending capture.

Point stimulation at 5×DPT never captured a single episode of the 72 attempted pacing events (Table 1). Point stimuli at 10×DPT captured 10% of the time. Line stimuli at 10×DPT (39%) captured significantly more often than 5×DPT (19%). The area captured per pacing train varied greatly, ranging from the minimum area counted as capture (40 mm$^2$) to almost the entire plaque (200 mm$^2$). The area captured was not static but could expand as the train proceeded so that an initially small area of capture could grow to cover most of the plaque. The converse was observed when the area of capture was large but then decreased as intrinsic VF activation fronts encroached.

Train order influenced capture rates. The first train captured 8% of the time, the second train captured significantly more frequently at 17%, and the third train also captured significantly more frequently than the first train at 26%.

Group 2: The pigs weighed 50.8±5.2 kg. The DPTs for 2 ms unipolar anodal, unipolar cathodal, and bipolar line stimuli were 22.8±4.6, 9.3±2.2, and 13.4±8.0 mA respectively. To ensure the plaque was in contact along the entire line the DPTs were also determined at five locations spread out along the line electrode. The cathodal DPTs for the electrodes at locations 2, 6, 12, 18, and 23 were 0.58±0.25, 0.60±0.31, 0.51±0.08, 0.42±0.10, and 0.68±0.31 mA respectively and were not significantly different.

The first pacing train was delivered 4.9±1.0 sec after the onset of VF and had a mean cycle length of 121.5±20.0 ms. The second train was initiated 11.6±1.8 sec after the VF was induced VF and had a mean cycle length of 115.3±14.7 ms, and the third train was delivered 17.4±1.9 sec after VF began and had a mean cycle length of 114.1±19.8 ms.

For unipolar cathodal pacing trains at 10×DPT the rate of capture was 61%; for unipolar anodal pacing trains at 10×DPT, 46%; for bipolar pacing trains at 10×DPT, 44%; for unipolar cathodal pacing trains at 16–33 times DPT (the strength of 10× the anodal DPT), 53%; and for bipolar pacing trains at 16–33×DPT, 51% (Table 2). There was no significant difference between the capture rates of the trains delivered at 10×DPT or greater than 10×DPT, nor at 10×DPT for the various stimulation polarities.

There was no significant difference amongst the pacing intervals for the trains delivered first, second, and third: 121.5±20.0 ms, 115.3±14.7 ms, and 114.1±19.8 ms, respectively. Train one had a capture rate of 11/61 or 18%, train two had 39/61 or 64%, and train three had 48/62 or 77%. The first train had significantly fewer capture episodes than the second or third trains. There was no difference between the two later trains. There was also no significant difference between the pacing rates of successful and unsuccessful pacing events.

In the one-second interval of VF immediately preceding those trains that captured, multiplicity and incidence of conduction block were significantly lower and repeatability was significantly higher (Table 3). The mean area swept out per activation front and the percent of wavefronts that appeared focally on the epicardium, possibly rising from breakthrough of intramural wavefronts to the epicardium, were not significantly different between the pacing trains which captured and those which did not.

The morphology of VF preceding trains one, two, and three was different (Table 3). The VF preceding train three had a significantly lower multiplicity than preceding either of the first two trains, but multiplicity before trains one and two was not different. VF before train three had significantly less block than before train one, while the incidence of block before train two was not different to either. VF preceding train two was significantly more repeatable than before train one, while VF preceding train three was significantly more repeatable than before both other trains. The fraction of wavefronts that arose in a focal/breakthrough pattern was significantly lower for train 3 than for both trains one and two, which were not significantly different. VF preceding the three trains was not significantly different regarding the area swept out per activation front.

The primary findings of the study are as follows. A line of electrodes is a more efficacious method of pacing the fibrillating heart than a point electrode. Increasing the strength to 10×DPT increases the rate of capture but exceeding this strength (particularly in the range of above 15, i.e., at 16–33 DPT) may not increase the rate of capture further. Pacing polarity does not seem to be a critical influence the ability of a pacing train from a line of electrodes to capture. Capture is more likely with the second and third trains than the first train. The more organized the VF prior to the onset of pacing, the greater the chance of capture.

Pacing trains delivered through a line of electrodes rather than a point electrode were significantly more able to capture VF. For point stimulation at 5×DPT, there were no capturing events, whereas the same relative strength for line stimulation had a 19% capture rate. A possible explanation for this is that the regions of the line that capture first are stimulated at greater than 5×DPT since the DPT is not constant along the line and the stimulus strength is 5×DPT for the region with the highest DPT. However, this is probably not the case, as the site of initial activation was not limited to a certain region of the line but occurred at various locations along the line. At 10×DPT line stimulation was able to capture four times more often than point stimulation. This may be because more tissue is stimulated with the line of electrodes, thus increasing the likelihood that the stimulus will encounter tissue during its excitable gap. Also, more total current is delivered to the line than the point electrodes for both 5×and 10×DPT stimulation, suggesting higher stimulus strength may influence the capture rate. However, there is actually less current delivered per individual electrode of the line than by the point electrode. Therefore, the line captures better with less current per electrode. This does not preclude the additive effects of the current over a large area during line stimulation. The virtual electrodes with a line stimulus may be considerably larger in both polarization magnitude and size, which may greatly affect the ability to capture. See Knisley et al., Line stimulation parallel to myofibers enhances regional uniformity of transmembrane voltage changes in rabbit hearts, Circ. Res. 1997;81:229–241.

Results from Group 1 indicate that the strength of the stimulus plays an important role in the ability of pacing stimuli to capture the fibrillating myocardium. Stimuli at 5×DPT were significantly less able to capture than at 10×DPT. In fact, point stimulation at 5×DPT was unable to capture at all, albeit that Allessie et al. and Kirchhof et al. found 6×DPT sufficient to capture fibrillating atria in dogs and KenKnight et al. found 5×DPT point stimuli sufficient in pig ventricles. The point electrode was larger and located in a different place than the electrodes in the KenKnight study, which may explain the difference in ability to capture with 5×DPT point stimulation. The line configuration was, however, able to capture at 5×DPT. Point stimulation at 10×DPT was able to capture 10% of the time, showing capture with bipolar point stimulation is possible. Line stimulation at 10×DPT captured significantly more often than 5×DPT. The reason for the increased efficacy could be due to the larger current strengths being better able to stimulate partially refractory tissue according to the classic strength—interval curve. See Wharton et al, Cardiac potential and potential gradient fields generated by single, combined, and sequential shocks during ventricular defibrillation, Circulation 1992; 85:1510–1523; Garcia-Calvo et al., The effects of selective stellate ganglion manipulation on ventricular refractoriness and excitability, Pacing and Clin. Electrophys. 1992; 15:1492–1503.

However, as shown in Group 2, the beneficial effects of increasing the stimulus current strength reaches a plateau. Increasing the strength to 16–33 times DPT for cathodal and bipolar stimulation did not increase capture efficacy. This suggests that in order to maximize pacing efficacy, one does not need exceed 10×–19×DPT. This finding is consistent with the classic hyperbolic strength-interval curve. Once the curve begins to approach an asymptote with the Y-axis, increasing stimulus strength no longer increases the ability to pace. It is possible that 10×DPT is near the asymptote (but the value could be higher for certain regions). Another possibility is that larger stimuli affect the myocardium in an adverse manner. Province et al. reported in perfused rabbit hearts that although larger stimuli increased the rate of capture, there was a decrease in the area they captured. See Province et al., Effect of pulse train amplitude and waveform on ability to entrain fibrillating rabbit ventricle with epicardial, Pacing and Clin. Electrophys. 1999; 22:A66 (Abstract).

The Group 2 study tested whether there was a difference in efficacy of the three stimulus modalities, i.e., unipolar anodal, unipolar cathodal, and bipolar. With stimuli set to 10×DPT, there was no difference in their abilities to capture. KenKnight et al. showed that bipolar pacing with a point electrode was more effective at capturing the fibrillating myocardium than either unipolar modality, between which there was no difference. See KenKnight et al., Regional capture of fibrillating ventricular myocardium: Evidence of an excitable gap, Circ. Res. 1995;77:849–855 This was not observed in the experiments. A possible explanation could be due to the testing line stimulation as opposed to point stimulation. In the case of line stimulation, the current is spread over a larger area and the membrane polarization is different than for point stimulation. See Knisley et al., Line stimulation parallel to myofibers enhances regional uniformity of transmembrane voltage changes in rabbit hearts, Circ. Res. 1997; 81:229–241.

There was no significant difference in the pacing rates for the three trains, nor was there a significant difference between pacing rates for the trains that captured and those that did not. This suggests that the intrinsic VF activation rate does not influence the ability of a pacing train to capture the myocardium. A possible explanation of this is that the tissue accommodates sufficiently to allow an excitable gap that is the same proportion of the cycle length regardless of the rate and the pacing algorithm was able to stimulate at the appropriate time regardless of rate.

For the one second interval preceding the onset of pacing, multiplicity, repeatability, and the percent of wavefronts that block during propagation were significantly different between those trains that did capture and those that did not. VF preceding successful trains had fewer individual pathways of activation that were more similar from activation to activation and experienced less conduction block within the mapped region. All these measures reflect an increase in the organization of VF. Organized VF may indicate a large excitable gap, making it easier for pacing to capture.

The duration of VF when pacing is performed plays a role in the likelihood of capture. The first train, delivered five seconds after VF onset, is least likely to capture. The second and third trains, delivered ten to twenty seconds into VF, are no different from each other in capture efficacy. It has long been known that VF changes over time. Wiggers reported almost seventy years ago that VF changes within the first few seconds. See Wiggers C. J., Studies of ventricular fibrillation caused by electric shock: Cinematographic and electrocardiographic observations of the natural process in the dog's heart: Its inhibition by potassium and the revival of coordinated beats by calcium, Am. Heart J. 1930;5:351–365. It also has been shown that quantitative descriptors of VF indicate the degree of organization early in VF increases in as VF progresses. See Rogers et al., A quantitative framework for analyzing epicardial activation patterns during ventricular fibrillation, Ann. Biomed. Eng. 1997; 25:749–760. There is also the possibility that pacing trains alter the substrate, the first train may prime the myocardium for the next pacing trains. A combination of these factors may be at work.

In combination with optical mapping techniques, pacing during VF could be used to elicit information regarding the excitable gap by allowing visualization of which portions of VF action potentials can and cannot be stimulated to initiate new activations that propagate. Clinically, there are at least two possible applications of pacing during fibrillation. One, it may be possible by pacing from several sites to halt fibrillation without giving a large defibrillation shock. This may pacing in a manner which captures sufficient tissue such that no reentrant circuits capable of maintaining fibrillation remain. To increase the likelihood of success, multi-site pacing may use pharmacological agents to increase the degree of organization so that pacing can capture larger regions or the number of reentrant circuits is reduced. Two, pacing during fibrillation may be combined with defibrillation to lower the strength of the shock needed to defibrillate.

DESCRIPTIONS OF EXPERIMENTAL ASSOCIATED FIGURES

FIGS. 13A and 13B illustrate the experimental preparation and the pacing train. Panel A (FIG. 13A) shows the location of the plaque on the right ventricular epicardial surface extending slightly over the LAD onto the LV. The plaque is comprised of 21 columns and 24 rows of electrodes 2 mm apart. The electrodes in column 11 were tied together and used as the unipolar line stimulation electrode. For bipolar stimulation, column 12 electrodes were also tied together and the stimulation was delivered through both columns. For bipolar point stimulation, electrodes in rows 11 and 12 of column 11 were used, indicated by X. The open circle in row 12 represents the sensing electrode for activation detection. FIG. 13B is a schematic of the pacing protocol. Approximately four seconds after VF initiation, the sensor function of the stimulator began activation detection (AD), from which the median was computed and taken as the intrinsic VF cycle length. Immediately after the last stimulus of the first and second trains, a new median activation interval was computed.

FIG. 14 shows snapshots of an activation front created by overdrive pacing with a line stimulus during normal sinus rhythm. Each snapshot is separated by 5 ms. The black horizontal line represents the line pacing electrode. The solid black snapshot represents the time of the pacing stimulus. Each pixel is a recording electrode site at which dV/dt was less than −0.5 V/sec during the interval for that frame. Dark gray pixels comprise activation fronts that arose from the pacing electrode. The activation fronts extend from the line in a linear manner indicating that capture occurred along the entire line.

FIG. 15 shows the 5 point first temporal derivative of a unipolar electrogram recorded from a captured region that is phase-locked with cathodal line pacing stimuli. The stimuli were delivered with a coupling interval of 94.5 ms, which represents 98% of the intrinsic preceding VF cycle length. The time-lapse between the stimulus and the local activation is due to the time taken to propagate from the pacing site to the recording electrode, and this time is constant because the time taken to traverse the same distance repeatedly does not change.

Figure 16:
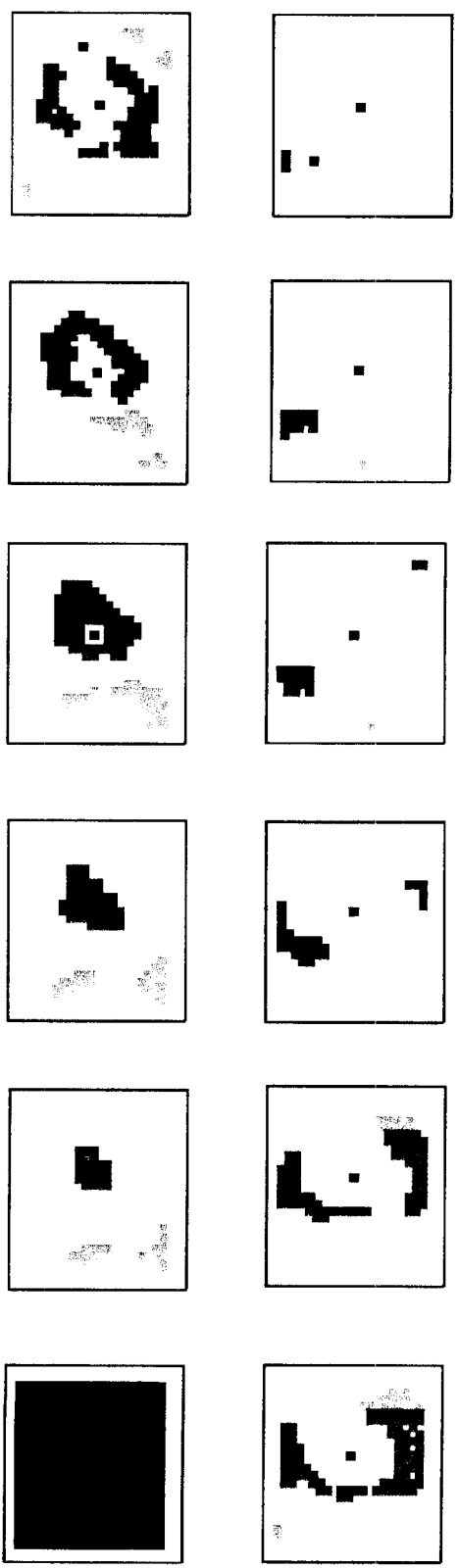
FIG. 16 is a series of screen printouts of activation fronts taken every 8 ms after a capturing 10×bipolar point stimulus during VF. The black central pixel represents the pacing site. The activation emanating from the point electrode (the dark gray pixels) does not form a complete ellipse as for overdrive pacing during sinus rhythm.
Figure 17A:
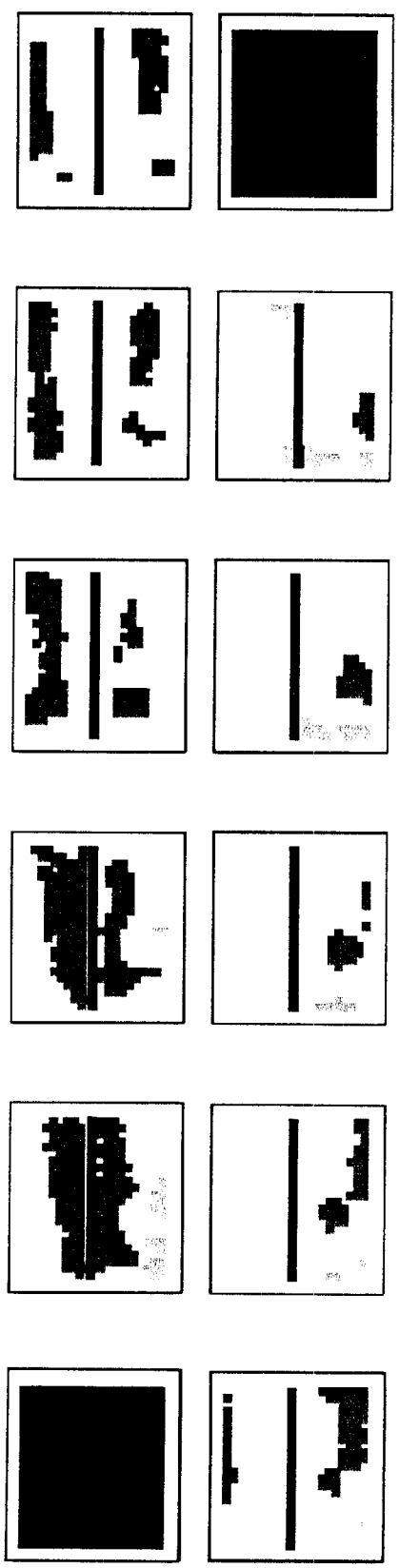
Figure 17B:
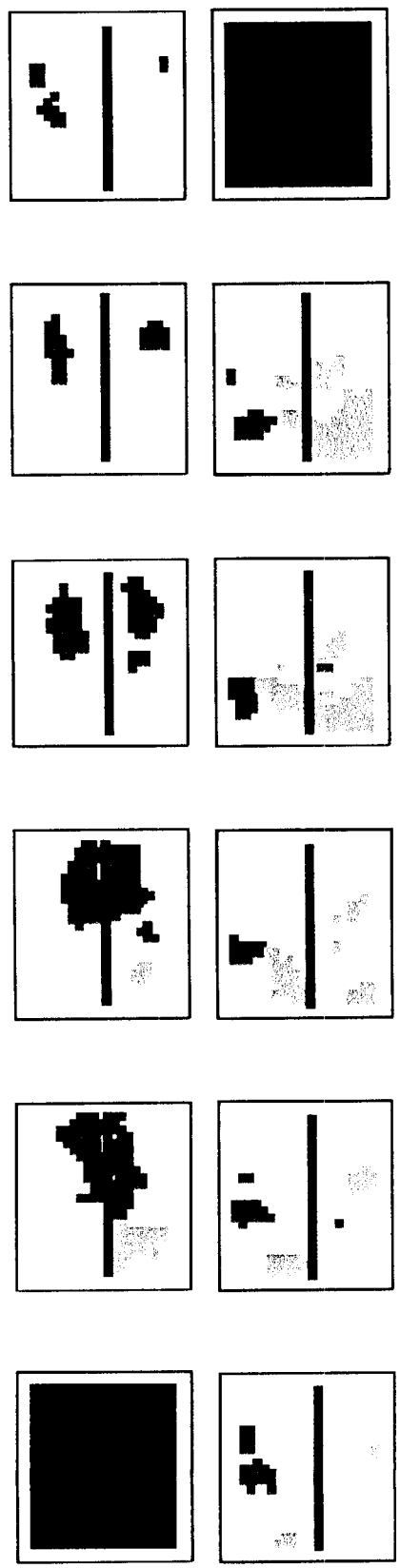

FIG. 16 shows snapshots every 8 ms of activation fronts after a capturing 10×bipolar point stimulus during VF. The black central pixel represents the pacing site. The activation emanating from the point electrode, the dark gray pixels, do not form a complete ellipse as for overdrive pacing during sinus rhythm. Owing to the dispersion in refractoriness and activation times during VF, the activation from the point electrode only spreads over excitable regions, so the ellipse is incomplete. If a region is activated by an intrinsic VF wavefront, the light gray pixels, and not the stimulus, then the stimulus-induced activation cannot propagate over that region.

In FIG. 17A of FIG. 17, activation fronts propagate away from the pacing line to activate almost the entire mapped region. In FIG. 17B, activation fronts propagate away from the right half of the pacing line (dark gray), but much of the left side of the mapped region is activated by an intrinsic VF activation front (light gray) entering from outside the mapped region. This activation front arrives at almost the same rate as but out of phase with the pacing stimuli so that the tissue it activates is refractory at the time of the stimulation. FIG. 17C depicts a pacing episode where there was no capture. The stimulus was delivered after an intrinsic wavefront has activated the area beneath the plaque and the tissue was refractory. The intrinsic activation (light gray) can be seen propagating beneath the electrode and thus the stimulus is not delivered during an excitable gap.

TABLE 1

Capture rates for treatments and trains in Group 1

|  | Animal 1 | Animal 2 | Animal 3 | Animal 4 | Total |
|---|---|---|---|---|---|
| Treatment |  |  |  |  |  |
| Line-10× DPT* | 1/18 | 4/18 | 11/18 | 12/18 | 28/72 |
| Line-5× DPT | 0/18 | 0/18 | 10/18 | 4/18 | 14/72 |
| Point-10× DPT† | 0/18 | 0/15 | 2/18 | 5/18 | 7/69 |
| Point-5× DPT | 0/18 | 0/18 | 0/18 | 0/18 | 0/72 |

TABLE 1-continued

Capture rates for treatments and trains in Group 1

|  | Animal 1 | Animal 2 | Animal 3 | Animal 4 | Total |
|---|---|---|---|---|---|
| Trains |  |  |  |  |  |
| 1 | 0/24 | 0/24 | 4/24 | 4/24 | 8/95 |
| 2‡ | 0/24 | 1/24 | 9/24 | 6/24 | 16/95 |
| 3‡ | 1/24 | 3/24 | 10/24 | 11/24 | 25/95 |

Ratios give number of episodes with capture divided by the total number of pacing episodes
*Line at ten times DPT is significantly different from line at five times DPT and point at five and ten times DPT
†point stimulation at ten time DPT is significantly different from point stimulation at five times DPT
‡Trains delivered second and third during a VF episode are significantly different from the first train delivered

TABLE 2

Capture rates for treatments and trains in Group 2

|  | Animal 5 | Animal 6 | Animal 7 | Animal 8 | Total |
|---|---|---|---|---|---|
| Treatment |  |  |  |  |  |
| Anode-10× DPT | 4/6 | 7/15 | 4/9 | 3/9 | 18/39 |
| Cathode-10× DPT | 4/6 | 9/15 | 3/8 | 7/9 | 23/38 |
| Bipole-10× DPT | 4/6 | 4/12 | 3/9 | 6/9 | 17/36 |
| Cathode-10× aDPT | 3/6 | 7/12 | 3/9 | 7/9 | 20/36 |
| Bipole-10× aDPT | 3/6 | 6/12 | 4/9 | 7/9 | 20/36 |
| Trains |  |  |  |  |  |
| 1 | 1/10 | 4/22 | 0/15 | 6/15 | 11/62 |
| 2* | 7/10 | 13/22 | 6/14 | 13/15 | 39/61 |
| 3* | 10/10 | 16/22 | 11/15 | 11/15 | 48/62 |

Ratios give number of episodes with capture divided by the total number of pacing episodes
aDPT denotes the current strength delivered was that of ten times the anodal DPT
*Trains delivered second and third during a VF episode are significantly different from the first train delivered

TABLE 3

Quantitative parameters of VF during the one second interval prior to the onset of pacing with a line electrode.

|  | Multiplicity | Repeatability | Fraction of Wavefronts that Blocked | by Wavefronts (mm2) | Fraction of Wavefronts that Breakthrough) |
|---|---|---|---|---|---|
| Outcome of Pacing Train |  |  |  |  |  |
| Capture | 4.9 ± 1.3* | 7.9 ± 2.8* | 0.30 ± 0.17* | 292 ± 121 | 0.42 ± 0.16 |
| Non Capture | 6.0 ± 1.7 | 6.0 ± 2.0 | 0.43 ± 0.15 | 266 ± 65 | 0.46 ± 0.13 |

TABLE 3-continued

Quantitative parameters of VF during the one second interval prior to the onset of pacing with a line electrode.

| | Multiplicity | Repeatability | Fraction of Wavefronts that Blocked | by Wavefronts (mm2) | Fraction of Wavefronts that Breakthrough) |
|---|---|---|---|---|---|
| Train Number | | | | | |
| 1 | 5.9 ± 1.6 | 5.7 ± 1.7** | 0.45 ± 0.15 | 262 ± 92 | 0.46 ± 0.14 |
| 2 | 5.5 ± 1.6 *** | 7.1 ± 2.9*** | 0.34 ± 0.17 | 282 ± 95 | 0.45 ± 0.14 *** |
| 3 | 4.9 ± 1.5**** | 8.2 ± 2.5**** | 0.30 ± 0.17**** | 296 ± 110 | 0.40 ± 0.15**** |

*The parameter for trains that captured is significantly different than for trains that did not capture
**Train 1 is significantly different than train 2
***Train 2 is significantly different than train 3
****Train 3 is significantly different than train 1

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of pacing to treat arrhythmia in a patient, comprising the steps of:
   positioning at least one electrode in a localized region of the heart of a patient such that it covers multiple proximate pacing sites over a distance of between about 0.25 cm–15 cm; and
   delivering a first pacing stimulation pulse train comprising a plurality of excitation pulses to the at least one electrode to the corresponding multiple pacing sites, to pace the myocardium of the patient.

2. A method according to claim 1, wherein the localized region of the heart is a localized region of the myocardium, and wherein the at least one electrode comprises an elongated line electrode having a contiguous electrical length and an electrode body which extends a distance of between about 0.25–15 cm so that, in position, said line electrode is in electrical communication with the desired localized region of the myocardium.

3. A method according to claim 1, wherein the at least one electrode comprises a plurality of discrete electrodes arranged in series and spaced apart and, in position, to occupy a length in the localized region of the heart in the range of between about 0.25 cm to 15 cm.

4. A method according to claim 3, wherein the plurality of proximate pacing sites are located in a desired localized region of the myocardium, and wherein said first delivering step comprises transmitting the excitation pulses to the plurality of discrete electrodes located about the localized region of the myocardium substantially concurrently.

5. A method according to claim 1, wherein the at least one electrode comprises a plurality of discrete electrodes arranged in parallel and spaced apart and, in position, to occupy a length in the localized region of the heart in the range of between about 0.25 cm to 15 cm.

6. A method according to claim 1, wherein said positioning step comprises positioning two line electrodes in the patient such that they are spaced apart a distance such that each resides in a different localized region of the heart.

7. A method according to claim 6, wherein each line electrode has at least about 10 discrete proximately spaced apart electrodes thereon.

8. A method according to claim 1, further comprising the step of sensing from at least one electrode positioned about the localized pacing region to measure cardiac activity.

9. A method according to claim 8, wherein the cardiac activity measured comprises identifying the length of the intrinsic activation rate of the localized region.

10. A method according to claim 8, wherein said sensing step comprises detecting the onset of a fibrillation event, and wherein said method further comprises the step of initiating said delivering step after the onset of the fibrillation event is detected.

11. A method according to claim 10, wherein said sensing step comprises detecting the return of substantially normal activity after said pacing stimulation; and said method comprises the step of terminating further delivery of pacing stimulation.

12. A method according to claim 8, wherein said sensing step detects whether the pacing stimulation is successful in capturing myocardium tissue.

13. A method according to claim 8, further comprising the step of adjusting the pacing stimulation pulse rate based on said sensing step.

14. A method according to claim 8, further comprising the adjusting selected parameters of the pacing stimulation pulse based on said sensing step.

15. A method according to claim 1, further comprising the steps of:
   sensing the cardiac cycle of the heart to assess at least one of the lengths of the interval between cardiac activation and the degree of organization of an arrhythmia; and
   delaying said delivering step until a substantially regular interval is indicated over at least 3 pulses.

16. A method according to claim 15, further comprising the step of administering a pharmacological agent to the patient to increase the degree of organization.

17. A method according to claim 1, wherein said at least one electrode comprises a plurality of spaced apart proximately mounted discrete electrodes held on a catheter.

18. A method according to claim 7, wherein said positioning step is carried out by inserting the catheter in the lumen of the heart.

19. A method according to claim 1, wherein said positioning step is carried out such that the at least one electrode is a positioned along a catheter which is threaded through the OS and inserted into a vein of the heart.

20. A method according to claim 1, wherein said positioning step is carried out so that the at least one electrode is positioned in the pericardial space.

21. A method according to claim 1, wherein said positioning step is carried out such that the at least one electrode is held inserted within one or more of the chambers of the heart such that the electrodes are held within a localized region of the myocardium.

22. A method according to claim 1, wherein said positioning step is carried out such that the at least one electrode is held along a desired localized region about the outer wall of the myocardium.

23. A method according to claim 1, wherein said positioning step is carried out such that the at least one electrode is positioned in the heart chambers and in the pericardial space.

24. A method according to claim 1, wherein said positioning step comprises positioning the at least one electrode in a localized region of the atria.

25. A method according to claim 1, wherein the at least one electrode is a plurality of electrodes, and wherein at least a portion of the electrodes are held together on a single line, such that, in position, the electrodes are placed against the atrial epicardium in the pericardial space.

26. A method according to claim 1, wherein the at least one electrode is positioned on a catheter which is positioned along the right side of the atrial septum or where the atrial septum intersects with the posterior atrial wall in the right atrium.

27. A method according to claim 1, wherein said positioning step is carried out so that the excitation pulses to the at least one electrode in the localized region is proximate at least one ventricle.

28. A method according to claim 1, wherein said positioning step comprises positioning two different line electrodes in the heart such that they are substantially parallel and positioned at least about 2–8 cm apart.

29. A method according to claim 28, wherein the two line electrodes are positioned between about 3 cm apart.

30. A method according to claim 1, wherein during fibrillation, said method further comprises the step of capturing a region of the fibrillating myocardium in the localized pacing region, the captured region having an area which is at least about 40 mm².

31. A method according to claim 30, wherein the captured region is at least about 100 mm².

32. A method according to claim 1, further comprising the steps of:
sensing the activation pattern of the electrical activity of the heart to identify regions susceptible to initiating arrhythmias; and
directing said first pacing train to at least one of the identified susceptible regions.

33. A method according to claim 1, wherein said positioning step is carried out such that the at least one electrode is located where refractory periods are relatively short.

34. A method according to claim 1, wherein said positioning step positions the at least one electrode where activation occurs rapidly during tachyarrhythmia.

35. A method according to claim 1, wherein said delivering step is carried out such that pacing is from a localized region of the atria.

36. A method according to claim 1, wherein said delivering step is carried out such that pacing is from a localized region about the left atrium near the pulmonary veins.

37. A method according to claim 1, wherein the localized region is in the ventricles.

38. A method according to claim 37, wherein the localized region is in the anterior and lateral basal two-thirds of the left ventricle.

39. A method according to claim 1, further comprising the step of capturing sufficient myocardium tissue such that the number of reentrant circuits capable of maintaining fibrillation are substantially reduced.

40. A method according to claim 1, further comprising the step of administering a pharmacological agent to the patient to increase the amount of tissue which is captured by said delivering step.

41. A method according to claim 1, wherein said first pacing train excitation pulses have an electrical strength which is above about five times a predetermined level associated with a diastolic pacing threshold used to establish a low level of electrical strength, said excitation pulses being configured so as to be able to stimulate a desired localized region in the myocardium.

42. A method according to claim 41, further comprising the step of establishing a diastolic pacing threshold level which is sufficient to stimulate a desired location in the myocardia of the patient prior to said first pacing step.

43. A method according to claim 1, further comprising the steps of measuring in situ the diastolic pacing threshold level of the patient in the localized region of the heart to establish a desired excitation pulse strength, and configuring the pacing train so that the excitation pulses provided by said first delivering step are between about 5–10 times above the determined diastolic pacing threshold.

44. A method according to claim 1, wherein said method comprises the step of delivering a defibrillation shock pulse to the patient during a fibrillation event proximate in time to said delivering step.

45. A method according to claim 44, wherein the first delivering step of pacing stimulation substantially captures the fibrillation in the weak effect portions of the myocardium, and wherein the shock strength associated with said defibrillation shock is decreased to a strength sufficient to halt fibrillation in the remaining portions of the myocardium not captured by the pacing stimulation.

46. A method according to claim 45, further comprising the step of synchronizing the defibrillation shock with respect to the pacing provided by at least said first and second delivering steps so that the defibrillation shock is inhibited from re-inducing fibrillation in the region captured by pacing.

47. A method according to claim 1, further comprising the step of delivering a second pacing train comprising a plurality of excitation pulses after said first pacing train to the plurality of sites.

48. A method according to claim 47, wherein said first and second pacing train excitation pulses are delivered such that each electrode generates an excitation current which averages less than about 2 mA per electrode.

49. A method according to claim 47, wherein said first and second pacing train excitation pulses are delivered such that said electrode is exposed to less than about 30 mA about the length thereof.

50. A method according to claim 47, wherein said at least one electrode comprises a plurality of discrete proximately arranged electrodes serially spaced apart, and wherein said first and second delivering steps comprise directing the respective excitation pulses substantially simultaneously to said electrodes.

51. A method according to claim 50, wherein said electrodes are configured to have a resistivity which is substantially equal to or greater than that of the myocardium.

52. A method according to claim 47, wherein said first and second delivering steps are carried out such that pacing is provided from a plurality of the pacing sites in the localized region of the myocardium substantially simultaneously.

53. A method according to claim 47, further comprising the step of delivering a third pacing train comprising a plurality of excitation pulses to the plurality of sites after said second delivering step.

54. A method according to claim 53, wherein said second and third delivering steps are each temporally delayed from the other delivering steps by a separation time period.

55. A method according to claim 53, wherein said first delivering step is carried out within about 5 seconds after onset of a fibrillating event.

56. A method according to claim 55, wherein said second delivering step is carried out within about 10 seconds after the onset of a fibrillating event.

57. A method according to claim 56, wherein said third delivering step is carried out within about 15–20 seconds after the onset of a fibrillating event.

58. A method according to claim 53, wherein at least one of said first, second, or third pacing trains has excitation pulses which have a higher electrical strength than the others.

59. A method according to claim 53, wherein each of the first, second, and third pacing trains comprises at least 3 pulses.

60. A method according to claim 53, wherein each of said pacing trains comprises between about 10–60 pulses, and wherein each of said pulses has a duration of between about 1–2 ms.

61. A pacing system for the heart of a subject, comprising:
 a pulse generator configured to generate at least one pacing stimulation pulse;
 a power source operably associated with said pulse generator; and
 at least one electrode operably associated with said pulse generator and adapted, in operational position, to reside about a localized region of the myocardium such that said at least one electrode extends over a distance of between about 0.25–15 cm thereof.

62. A pacing system according to claim 61, wherein said at least one electrode is a plurality of discrete electrodes arranged on one lead line.

63. A pacing system according to claim 61, wherein said at least one electrode is an elongated electrode having a contiguous body with a length of between about 0.25–15 cm.

64. A pacing system according to claim 61, wherein said at least one electrode is configured with a resistivity of greater than about 100 Ω/cm.

65. A pacing system according to claim 61, wherein said at least one electrode is arranged to transmit the pacing train stimuli to the myocardium at different sites within a localized region substantially concurrently.

66. A pacing system according to claim 65, wherein said electrode pairs are two line electrodes held on two substantially parallel spaced apart line electrodes which are independently electrically operable and positioned in at least one localized region of the heart so that the electrodes contact the myocardium thereat.

67. A pacing system according to claim 66, wherein said at least one electrode comprises corresponding first and second electrode pairs, and wherein, in position, the electrode pairs are arranged to be spaced apart a distance of between about 2–8 cm.

68. A pacing system according to claim 61, further comprising at least one sensing electrode configured to detect the cardiac activity of the localized region of the heart.

69. A pacing system according to claim 68, further comprising a cardiac cycle monitor and a controller, and wherein the system is configured to adjust or control selected operational parameters of the pacing stimulus which is directed to said at least one electrode based on the cardiac activity sensed by said at least one sensor.

70. A pacing system according to claim 69, wherein the selected operational parameters includes determining when to terminate the pacing stimulus transmitted to the electrodes.

71. A pacing system according to claim 69, wherein the selected operational parameters includes determining the appropriate stimulation strength of between about 5–10 times an in situ measured DPT.

72. A pacing system according to claim 69, wherein the selected operational parameters includes determining whether a regular interval exists.

73. A pacing system according to claim 72, wherein the system is configured to delay transmittal of the pacing stimulus to the localized region until a desired regular-interval is indicated.

74. A pacing system according to claim 69, wherein the operational parameters include at least one of pacing rate, pulse duration, and strength.

75. A pacing system according to claim 69, wherein the sensor is able to detect the degree of capture associated with a pacing stimulus based on the sensed cardiac activity.

* * * * *